US010759722B2

(12) United States Patent
Marker et al.

(10) Patent No.: US 10,759,722 B2
(45) Date of Patent: Sep. 1, 2020

(54) PRODUCTION OF LIQUIDS AND REDUCED SULFUR GASEOUS PRODUCTS FROM SOUR NATURAL GAS

(71) Applicant: Gas Technology Institute, Des Plaines, IL (US)

(72) Inventors: Terry Marker, Palos Heights, IL (US); Jim Wangerow, Oak Park, IL (US); Dane Boysen, Anchorage, AK (US); Martin B. Linck, Roscoe, IL (US); Pedro Ortiz-Toral, Wheeling, IL (US)

(73) Assignee: Gas Technology Institute, Des Plaines, IL (US)

( * ) Notice: Subject to any disclaimer, the term of this patent is extended or adjusted under 35 U.S.C. 154(b) by 0 days.

(21) Appl. No.: 15/867,902

(22) Filed: Jan. 11, 2018

(65) Prior Publication Data
US 2019/0210941 A1    Jul. 11, 2019

(51) Int. Cl.
*C07C 2/76* (2006.01)
*C10L 3/10* (2006.01)
(Continued)

(52) U.S. Cl.
CPC ............... *C07C 2/76* (2013.01); *C07C 2/08* (2013.01); *C07C 2/42* (2013.01); *C10L 3/103* (2013.01);
(Continued)

(58) Field of Classification Search
None
See application file for complete search history.

(56) References Cited

U.S. PATENT DOCUMENTS

| 1,907,274 A * | 5/1933 | Wheeler ............... C07C 2/00 423/443 |
| 4,451,685 A | 5/1984 | Nevitt et al. |

(Continued)

OTHER PUBLICATIONS

Zhu, Q. et al., "Sulfur as a selective 'soft' oxidant for catalytic methane conversion probed by experiment and theory", Nature Chemistry, vol. 5, pp. 104-109, (Dec. 2012).
(Continued)

Primary Examiner — In Suk C Bullock
Assistant Examiner — Alyssa L Cepluch
(74) Attorney, Agent, or Firm — Banner & Witcoff, Ltd.

(57) ABSTRACT

Aspects of the invention are associated with the discovery of approaches for the conversion of sour natural gas streams, by conversion to liquid hydrocarbons. Particular processes and their associated apparatuses advantageously combine (i) dehydroaromatization (DHA) of methane in a gaseous feedstock, to produce aromatic hydrocarbons such as benzene, with (ii) the reaction of $H_2S$ and methane in this feedstock, to produce organic sulfur compounds such as carbon disulfide ($CS_2$) and thiophene ($C_4H_4S$). A gaseous product having a reduced concentration of $H_2S$ is thereby generated. The aromatic hydrocarbons and organic sulfur compounds may be recovered in a liquid product. Both the gaseous and liquid products may be easily amenable to further upgrading. Other advantages of the disclosed processes and apparatuses reside in their simplicity, whereby the associated streams, including a potential gaseous recycle, generally avoid high partial pressures of $H_2S$.

19 Claims, 11 Drawing Sheets

(51) Int. Cl.
*C07C 2/42* (2006.01)
*C07C 2/08* (2006.01)

(52) U.S. Cl.
CPC .... *C07C 2521/04* (2013.01); *C07C 2523/882* (2013.01); *C07C 2527/051* (2013.01); *C10L 2290/10* (2013.01); *C10L 2290/542* (2013.01); *C10L 2290/548* (2013.01)

(56) References Cited

U.S. PATENT DOCUMENTS

| | | | |
|---|---|---|---|
| 4,480,143 A | 10/1984 | Chang et al. | |
| 4,543,434 A | 9/1985 | Chang | |
| 4,822,938 A | 4/1989 | Audeh et al. | |
| 4,864,074 A | 9/1989 | Han et al. | |
| 5,043,505 A | 8/1991 | Erekson et al. | |
| 7,772,450 B2* | 8/2010 | Iaccino | C01B 3/38 518/703 |
| 8,378,162 B2* | 2/2013 | Iaccino | B01J 29/48 518/700 |
| 8,915,981 B2 | 12/2014 | Marker et al. | |
| 8,981,169 B2* | 3/2015 | Iaccino | C07C 2/76 585/407 |
| 2017/0088489 A1* | 3/2017 | Salciccioli | C07C 7/04 |
| 2017/0088779 A1* | 3/2017 | Stauffer, II | C10G 1/002 |
| 2018/0186707 A1* | 7/2018 | Abudawoud | B01J 19/24 |

OTHER PUBLICATIONS

Quann, R.J. et al., "Chemistry of Olefin Oligomerization over ZSM-5 Catalyst", Ind. Eng. Chem. Res., vol. 27(4), pp. 565-570, (1988).

Fukuda, K. et al., "Catalytic Decomposition of Hydrogen Sulfide", Ind. Eng. Chem. Fundam., vol. 17(4), pp. 243-248 (1978).

Hosseini, H. et al., "Carbon Disulfide Production via Hydrogen Sulfide Methane Reformation", International Scholarly and Scientific Research & Innovation, vol. 4(2), pp. 198-201 (2010).

Erekson, E.J. "Gasoline From Natural Gas by Sulfur Processing", Technical Report, Work Performed Under Contract No. DE-AC22-93PC92114, (Jul. 1996).

* cited by examiner

PRODUCTION OF LIQUIDS AND REDUCED SULFUR GASEOUS PRODUCTS FROM SOUR NATURAL GAS

STATEMENT REGARDING FEDERALLY SPONSORED RESEARCH OR DEVELOPMENT

This invention was made with government support under U.S. Department of Energy Award DE-AR0000761. The government has certain rights in the invention.

FIELD OF THE INVENTION

Aspects of the invention relate to processes and systems for the conversion of sour methane (e.g., a feedstock comprising methane and $H_2S$), optionally comprising other hydrocarbons such as ethane and/or propane, by a number of possible reactions, including soft oxidation and dehydroaromatization, to produce a higher value gaseous product having a reduced concentration of $H_2S$ and a liquid product comprising aromatic hydrocarbons and organic sulfur compounds. If necessary, downstream sulfur removal from either the gaseous product or liquid product can be achieved in an economical manner.

DESCRIPTION OF RELATED ART

The ongoing search for alternatives to crude oil, for the production of hydrocarbon fuels and specialty chemicals (e.g., petrochemical precursors such as olefins and aromatics), is increasingly driven by a number of factors. These include diminishing petroleum reserves, higher anticipated energy demands, and heightened concerns over greenhouse gas (GHG) emissions from sources of non-renewable carbon. In view of its abundance in natural gas reserves, methane has become the focus of a number of possible synthesis routes. Known commercial processes for converting natural gas into liquid fuels include (i) reforming to generate a CO- and $H_2$-containing syngas, followed Fisher-Tropsch (FT) synthesis, and (ii) the formation of methanol as an intermediate for subsequent dehydration, i.e., in methanol-to-gasoline (MTG) conversion. Whereas these methods are widely used and improve the economics of transporting natural gas over long distances, they nonetheless involve considerable complexity, capital expenditure, and multiple conversion steps. These known methods also suffer from poor selectively to gasoline boiling-range hydrocarbons and result in the production of carbon dioxide. Furthermore, both FT and MTG processes require pretreatment of the feedstock for $H_2S$ removal, in order to obtain acceptable catalyst stability.

The oxidation of methane with $O_2$ to directly produce hydrocarbons and $H_2O$, while studied extensively, has been met with a number of significant challenges. These include thermodyamically favorable reaction pathways that lead to further oxidation ("over oxidation") of the desired hydrocarbons and oxygenates, resulting in substantial $CO_2$ formation. In addition, management of the highly exothermic oxidation reaction poses a number of practical problems in terms of process design. The catalytic, oxidative coupling of methane and other hydrocarbons to form higher hydrocarbons is described, for example in U.S. Pat. No. 5,043,505.

In comparison, the free energy losses associated with the counterpart reactions using $S_2$ versus $O_2$ as a reactant with methane, including over oxidation reactions, are significantly lower. This has led to the characterization of sulfur-based methane conversion as "soft oxidation." The study of various catalysts for the conversion of $CH_4$ and elemental sulfur to $CS_2$ and hydrocarbons is documented, for example, in Zhu, Q. et al. (NATURE CHEMISTRY, Vol. 5 (December 2012): 104-109). Other publications disclosing the production of $CS_2$ from methane and sulfur include U.S. Pat. Nos. 4,480,143; 4,543,434; 4,822,938; and 4,864,074, which also describe further processing steps to obtain higher hydrocarbons such as aromatics. See also Quann, R. J. et al. (IND. ENG. CHEM. RES., Vol. 27(4) (1988): 565-570) and U.S. Pat. No. 4,451,685. The use of $S_2$ over $O_2$ has therefore been investigated as a route to hydrocarbon production, in which the product selectivity and process thermodynamics are more easily managed. In addition, methods for obtaining elemental sulfur as a necessary starting material are practiced industrially as the Claus process, or are otherwise known from, for example, Fukuda, K. et al, (IND. ENG. CHEM. FUNDAM., Vol. 17(4) (1978): 243-248). Sulfur is also a less expensive oxidant than oxygen, since oxygen must be initially separated from nitrogen for use.

More recently, the use of $H_2S$, rather than elemental sulfur, has been investigated as the reactant for catalytically converting $CH_4$ to $CS_2$. See Hosseini, H. et al. (INTERNATIONAL SCHOLARLY AND SCIENTIFIC RESEARCH & INNOVATION, Vol. 4(2) (2010): 198-201). An additional downstream, catalytic reaction of the $CS_2$, as part of a two-step hydrogen sulfide methane ("HSM") process for producing hydrocarbons, is discussed in Erekson, E. J. (Work Performed Under Contract No.: DE-AC22-93PC92114 (July 1996)). In order for processes that synthesize liquid hydrocarbons (e.g., gasoline and jet fuel) from methane to advance to the point of economic feasibility, a number of factors must be addressed, particularly in terms of product yields and process integration steps that limit the losses of valuable reactants and intermediates. Proposals for producing hydrocarbons according to such synthesis routes are described in US 2017/0101352.

Currently, there are many situations in which waste gases having heating value, for example certain gases generated in oil refining and other operations at low or moderate volumetric flow rates, are flared. In some cases, electricity can be recovered in connection with combusting these gases, using a turbine or engine with electricity generating equipment. However, such apparatuses for supplying electricity to a power grid typically specify low concentrations of $H_2S$ in the gases to be combusted, making $H_2S$ removal a necessity for many potential feeds. If such purification involving $H_2S$ removal from methane (i.e., "sweetening") uses adsorbent technology, this can become quite costly for "sour" gas streams having $H_2S$ levels above 1 vol-%, to the extent that this contamination level effectively serves as a financial barrier for the purpose of electricity generation. As a result, this sour methane-containing gas is typically flared, producing $SO_2$ as well as $CO_2$ emissions.

In cases of producing large volumes of $H_2S$-contaminated gas, centralized gas processing facilities can utilize amine solvent separation, combined with the Claus process (Amine/Claus), to produce elemental sulfur. The financial feasibility of such sulfur recovery complexes, however, requires very high volumes of gas with significant $H_2S$ concentrations. Smaller quanties of sour gas can be economically processed in this manner, only if such a centralized gas processing facility is geographically accessible. Otherwise, there is currently no commercially attractive option for treating sour gas produced at low to medium volumes and/or with moderate $H_2S$ concentrations, such that the art of gas processing would benefit greatly if a financially viable solution were realized.

SUMMARY OF THE INVENTION

Aspects of the invention are associated with the discovery of fundamentally superior approaches to the monetization of sour natural gas streams, by conversion to liquid hydrocarbons. Conventionally, this has been undertaken by first removing the $H_2S$, rendering the sweetened natural gas suitable for catalytic reforming to produce syngas, followed by Fischer-Tropsch synthesis to generate hydrocarbons of a higher carbon number, suitable for use in liquid fuels. However, each step in this conventional gas-to-liquids process adds significant complexity and cost. In searching for potential routes to liquid hydrocarbon production via the soft oxidation of methane with $H_2S$, the inventors discovered catalyst systems and operating parameters whereby the soft oxidation product carbon disulfide ($CS_2$) is generated, in combination with significant yields of aromatic hydrocarbons such as benzene ($C_6H_6$) as a liquid product, in addition to ethylene ($C_2H_4$) as a gaseous product.

Associated with this discovery, processes as described herein present a simple solution, whereby sour natural gas or, more generally, feedstocks comprising predominantly methane and minor amounts of $H_2S$, are "sweetened" by the generation of a methane-containing gaseous product stream with a reduced $H_2S$ concentration. This significantly improves the value of the gaseous product stream relative to the feedstock, for example by rendering this gaseous product suitable for applications involving its combustion, such as electricity generation as described above.

Also produced is a liquid product comprising valuable components, including aromatic hydrocarbons, in combination with organic sulfur compounds. This ability to readily convert gaseous sulfur contaminants, in the form of $H_2S$, to liquid sulfur contaminants in the liquid product, presents financially attractive options in terms of the transport and ultimate removal of sulfur. Advantageously, for example, sulfur compounds present in liquid form, together with liquid hydrocarbons, may be easily provided to, and blended with, refinery hydroprocessing (e.g., hydrotreating/hydrodesulfurization) feeds. Hydroprocessing then converts the liquid organic sulfur compounds to $H_2S$ at the refinery site, which may benefit from having a Claus facility for elemental sulfur production, by treatment of a combined hydroprocessing gas effluent that in this case is generated at the refinery scale. Aspects of the invention therefore relate to downstream integration with refinery hydroprocessing operations, for example following the transport of the liquid product as described herein for addition to (e.g., blending with) a refinery hydrodesulfurization feedstock (e.g., a middle distillate such as a diesel boiling-range hydrocarbon fraction, a heavy distillate such as vacuum gas oil, or light cycle oil) and co-processing with such feedstock for sulfur removal, in order to exploit a favorable economy of operation on an industrial (refinery) scale.

Particular aspects of the invention relate to processes that advantageously combine (i) dehydroaromatization (DHA) of methane in a gaseous feedstock, to produce aromatic hydrocarbons such as benzene, with (ii) the reaction of $H_2S$ and methane in this feedstock, to produce organic sulfur compounds such as carbon disulfide ($CS_2$) and thiophene ($C_4H_4S$). The aromatic hydrocarbons and organic sulfur compounds are obtained in a liquid product recovered from the process. Single-pass yields of the aromatic hydrocarbons may be improved by the presence of higher molecular weight hydrocarbons (e.g., ethane and propane) in the gaseous feedstock. Further advantages of the disclosed processes reside in their simplicity, whereby the streams, including a potential gaseous recycle, do not involve high partial pressures of $H_2S$ and/or temperatures conventionally used in soft oxidation, which would otherwise mandate special precautions in terms of materials/metallurgy and overall safety. Processes described herein therefore offer a straightforward solution for the removal of sulfur from sour natural gas, which may overcome the need for $H_2S$-selective adsorbents and their disposal. In fact, $H_2S$ in these processes acts as a reactant in the methane-containing feedstock, as opposed to solely a contaminant requiring removal.

Therefore, in addition to producing a high value liquid product containing, in the form of organic sulfur components, a significant portion of the sulfur initially contained in the sour natural gas, processes described herein can simultaneously produce an upgraded and higher value (sweetened) methane-containing gaseous product. These valuable gaseous and liquid product streams can be provided using simple apparatuses for carrying out methane DHA and sweetening through soft oxidation. Due to their simplicity, these apparatuses may be made transportable (e.g., skid mounted), such that they may be conveyed to sites where they are effectively utilized, including sources of sour natural gas (e.g., wellhead gas) or $H_2S$-contaminated methane generally. Such sources are often "stranded," meaning they lack access to a suitable facility for conversion to value-added products and are therefore generally flared (combusted). Processes described herein can effectively monetize such otherwise unusable sources of sour natural gas, with the added benefit of reducing $SO_2$ emissions by capturing sulfur in liquid form.

Embodiments of the invention are directed to a methane DHA process comprising contacting a feedstock comprising methane and $H_2S$ with a DHA catalyst and recovering a liquid product comprising, as conversion products of the methane and $H_2S$, one or more aromatic hydrocarbons and one or more sulfur compounds. In a representative feedstock, the methane is present at a concentration of at least about 50 vol-%, such that methane is generally the predominant component of this feedstock on a volumetric or molar basis. The $H_2S$ may be present in the feedstock as a minor component on a volumetric or molar basis, for example at a concentration from about 1 vol-% to about 25 vol-%. Further embodiments are directed to a process for sweetening of (or removal of $H_2S$ from) a feedstock comprising methane and $H_2S$. The process comprises (a) in a DHA reaction stage, contacting at least a portion of the feedstock with a DHA catalyst, to provide a DHA effluent, and (b) in a separation stage (e.g., a gas/liquid separation stage), separating from at least a portion of the DHA effluent (i) a liquid product comprising, as conversion products of the methane and $H_2S$, one or more aromatic hydrocarbons and one or more organic sulfur compounds, and (ii) a methane-containing gaseous product. The DHA reaction stage may be advantageously carried out at low pressure, such as an absolute pressure from about 100 kPa to about 300 kPa.

Yet further embodiments are directed to apparatuses and their associated equipment, for producing aromatic hydrocarbons from methane, together with a sweetened gaseous product stream, as described above. Representative systems comprise a dehydroaromatization (DHA) reactor configured to connect, via a system input, to a source of a methane-containing fresh feed (e.g., sour natural gas). A separator may be configured to receive a DHA effluent from the DHA reactor and also configured to provide (i) via a system liquid outlet, a liquid product comprising one or more aromatic hydrocarbons and one or more organic sulfur compounds, and (ii) a methane-containing gaseous product. According to a particular embodiment, an intermediate ethylene oligomerization (EO) reactor, disposed between the DHA reactor and the separator, may be configured to receive the DHA effluent, prior to this effluent being received by the separator.

These and other embodiments, aspects, and advantages relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures.

The figures should be understood to present an illustration of the disclosure and/or principles involved. In order to facilitate explanation and understanding, simplified equipment is depicted in the schematic illustrations of FIGS. 1 and 2, and these figures are not necessarily drawn to scale, such that some components and structures, as well details pertaining to their configurations, may be exaggerated. Valves, instrumentation, and other equipment and systems not essential to the understanding of the various aspects of the invention are not shown. As is readily apparent to one of skill in the art having knowledge of the present disclosure, processes for converting a methane-containing feedstock to higher value gaseous and liquid products will have configurations and components determined, in part, by their specific use. In FIGS. 1 and 2, the same reference numbers are used to identify the same or similar features.

DETAILED DESCRIPTION

Figure 1:
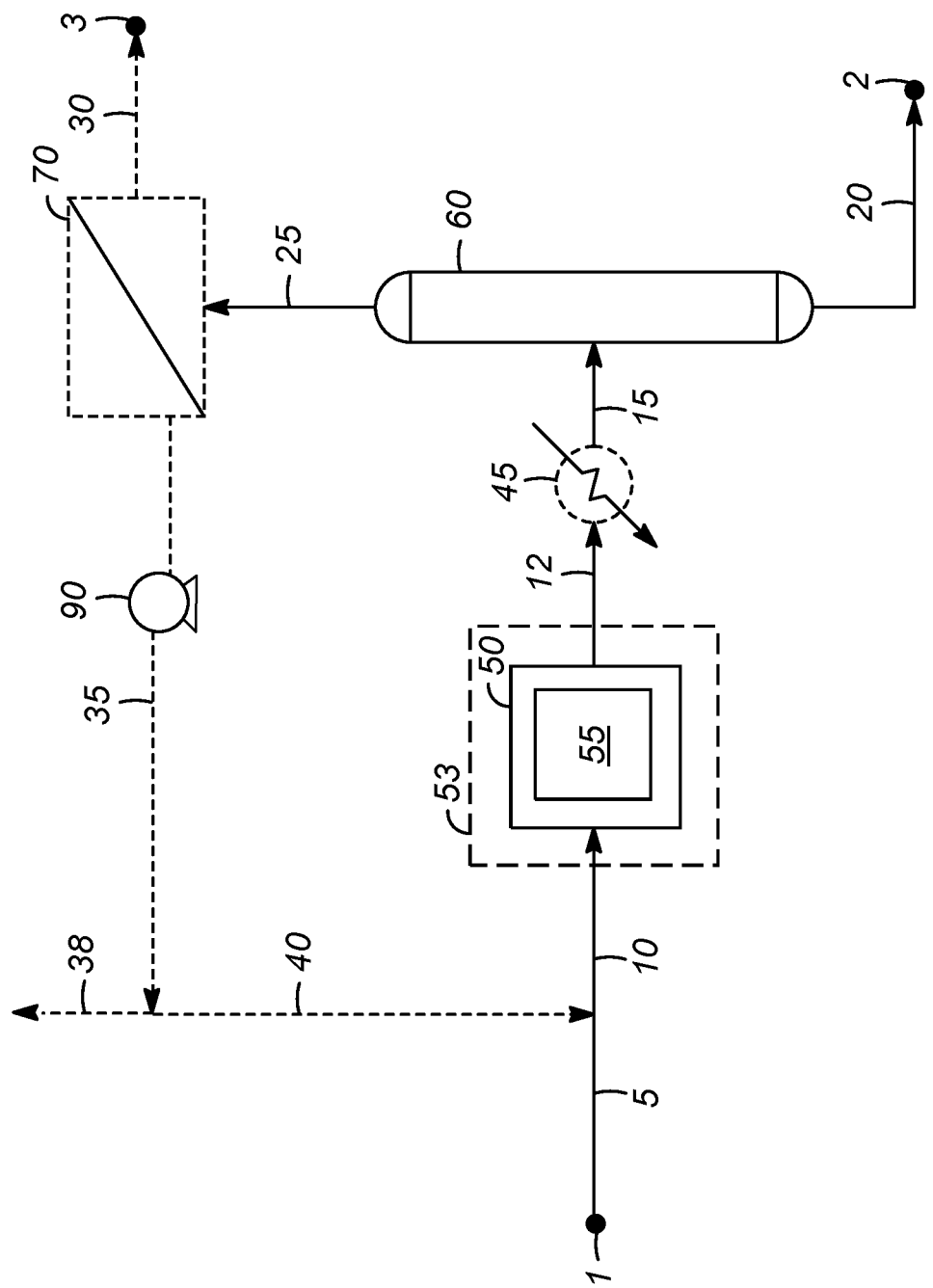
FIG. 1 depicts a flowscheme that illustrates a representative process as described herein, comprising a single methane dehydroaromatization (DHA) reaction stage.

The expressions "wt-%" and "vol-%," are used herein to designate weight percentages and volume percentages, respectively. The expressions "wt-ppm" and "vol-ppm" are used to designate weight parts per million and volume parts per million, respectively. Concentrations of liquid phase components are generally reported in terms of wt-% (or wt-ppm), whereas concentrations of gas phase components are generally reported in terms of vol-% (or vol-ppm). For ideal gases, "vol-%" is equal to molar percentage and vol-ppm is equal to molar parts per million.

Embodiments of the invention relate to a methane dehydroaromatization (DHA) process for converting a feedstock comprising methane and $H_2S$ to a liquid product comprising, as conversion products of the methane and/or $H_2S$, a hydrocarbon such as an aromatic hydrocarbon, in addition to an organic sulfur compound, such as a thiophene or alkyl thiophene. The liquid product is normally recovered separately from a gaseous product comprising unconverted methane (e.g., methane that is not converted to hydrocarbons by DHA). This recovery may be carried out in a single stage of vapor-liquid (flash) separation, to resolve the gaseous and liquid products, comprising, for example, components boiling below room temperature and above room temperature, respectively. Alternatively, multiple vapor-liquid equilibrium stages of separation may be performed, for example, using a distillation column to resolve products with more defined compositions and/or component boiling point cutoffs. Separation can also be performed with the inclusion of a stripping vapor stream or stripping liquid stream, having affinity for (e.g., acting as a preferential solvent of) one or more components and thereby influencing the materialization of such component(s) in either the gaseous or liquid product.

Feedstocks

Representative feedstocks comprising methane and $H_2S$ are gases comprising at least about 50 vol-% (e.g., from about 50 vol-% to more than 99 vol-%) $CH_4$, with such gases typically comprising at least about 75 vol-% (e.g., from about 75 vol-% to more than 99 vol-%) $CH_4$, and often comprising at least about 90 vol-% (e.g., from about 90 vol-% to more than 99 vol-%) $CH_4$. Methane-containing feedstocks are "sour" in view of their $H_2S$ content, which may range generally from about 0.1 vol-% (i.e., 1000 vol-ppm) to about 25 vol-%. This upper concentration, or even higher concentrations, may be attained, for example, in the case of processes utilizing a methane-containing gaseous recycle, whereby the methane-containing feedstock may be provided to a DHA reaction stage as a combination of a methane-containing fresh feed and the methane-containing gaseous recycle, which may contain a significant concentration of $H_2S$, by virtue of its separation from an $H_2S$-depleted methane product. Representative methane-containing feedstocks in such recycle operation may range typically from about 1 vol-% to about 15 vol-% and often from about 2 vol-% to about 12 vol-%. Methane-containing fresh feeds (e.g., sources of sour natural gas) used in such recycle operation, or otherwise used in once-through operation and therefore in this case equating to the "feedstock comprising methane and $H_2S$," as described herein, may comprise $H_2S$ generally in an amount from about 0.1 vol-% to about 10 vol-%, typically from about 0.1 vol-% to about 8 vol-%, and often from about 0.5 vol-% to about 5 vol-%. Advantageously, $H_2S$ is a reactant in the process, as opposed to a contaminant requiring costly removal techniques to prevent the poisoning of catalysts used in known processes, such as FT synthesis and MTG conversion, referenced above.

As can be appreciated from the above description, $H_2S$ is generally present in the "methane-containing fresh feed" (e.g., in the case of recycle operation) or a "feedstock comprising methane and $H_2S$" (e.g., in the case of either recycle or once-through operation), and more particularly present in the gas being contacted with a DHA catalyst (e.g., contained in a DHA reactor), such that $H_2S$ is well below the stoichiometric 2:1 $H_2S$:$CH_4$ molar ratio, according to the soft oxidation reaction of these components, namely:

$$2H_2S+CH_4 \rightarrow CS_2+4H_2.$$

Representative $H_2S$:$CH_4$ molar ratios are generally less than about 1:1 (e.g., from about 0.005:1 to about 1:1), typically less than about 0.5:1 (e.g., from about 0.01 to about 0.5:1), and often less than about 0.2:1 (e.g., from about 0.02:1 to about 0.2:1), consistent with the objective of converting only a portion of the methane, with greater emphasis on converting the stoichiometrically-limited $H_2S$ to organic sulfur compounds in the recovered liquid product. Such low $H_2S$:$CH_4$ molar ratios are also advantageous from the standpoint of reactor metallurgy, which is generally less susceptible to failure when $H_2S$ content, and particularly $H_2S$ partial pressure, is reduced.

A "methane-containing fresh feed" or a "feedstock comprising methane and $H_2S$" may further comprise light hydrocarbons such as ethane and propane, which have been found to react under methane DHA conditions and are in fact believed to contribute to the yield of hydrocarbons in the liquid product. In particular, ethane and/or propane are believed to more readily undergo aromatization (by conversion at lower temperature) to form aromatic hydrocarbons, relative to methane. Ethane and/or propane may be present at a concentration, or combined concentration if both components are present, from about 0.1 vol-% to about 10 vol-% or from about 1 vol-% to about 5 vol-%. Higher concentrations of ethane and/or propane, although typically not present in natural gas, are not detrimental to the process. The methane-containing fresh feed, or feedstock comprising methane and $H_2S$, may further comprise non-hydrocarbon impurities such as CO and $CO_2$, for example in typical quantities found in sources of natural gas. CO and/or $CO_2$ may be present at a concentration, or combined concentration if both components are present, from about 1 vol-% to about 15 vol-% or from about 3 vol-% to about 10 vol-%.

An important methane-containing fresh feed, or feedstock comprising methane and $H_2S$, is sour natural gas, and particularly in the form of stranded natural gas, which, using known processes, cannot be economically upgraded to liquid hydrocarbons. Sour natural gas, according to particular embodiments, may comprise at least about 60 vol-% methane and at most about 10 vol-% of $H_2S$. Other of such sources of methane may be obtained from coal or biomass (e.g., char) gasification, from a biomass digester, or as an effluents from biofuel production processes (e.g., pyrolysis processes, including hydropyrolysis processes, and fatty acid/triglyceride hydroconversion processes). The methane may therefore be derived from a renewable carbon source. Other sources of methane, in a methane-containing fresh feed, or a feedstock comprising methane and $H_2S$, may include effluents of industrial processes such as steel manufacturing processes or non-ferrous product manufacturing processes. Further sources include effluents of petroleum refining processes, electric power production processes, chemical (e.g., methanol) production processes, and coke manufacturing processes.

Dehydroaromatization Process/Conditions/Catalysts

Processes described herein convert methane and $H_2S$, in one or more reaction stages or steps that include a DHA reaction stage or step, to conversion products that boil above room temperature (20° C.), that may consequently be recovered (e.g., by condensation) into a liquid product. Representative conversion products include one or more aromatic hydrocarbons, such as benzene, toluene, xylenes (e.g., any of its isomers ortho-xylene, meta-xylene, or para-xylene), and other alkylbenzenes (e.g., ethylbenzene). Polycyclic aromatic hydrocarbons, such as naphthalene, may also contribute to the aromatic hydrocarbon content of the liquid product. Often, aromatic hydrocarbons such as benzene and naphthalene represent a large proportion, such as greater than 90 wt-% or even greater than 95 wt-%, of all hydrocarbons in the liquid product. Other conversion products that may be recovered in the liquid product, and in this case obtained from the conversion of $H_2S$, include organic sulfur compounds such as disulfides, including carbon disulfide ($CS_2$) and alkyl disulfides (e.g., dimethyldisulfide), as well as thiols, including alkylthiols (e.g., ethanethiol). Organic sulfur compounds resulting from aromatization further include thiophenes, such as thiophene ($C_4H_4S$) and alkyl thiophenes (e.g., methylthiophenes and ethylthiophenes). Often, carbon disulfide and thiophene represent a large proportion, such as greater than 90 wt-% or even greater than 95 wt-%, of all organic sulfur compounds in the liquid product.

The DHA catalyst, used to carry out the conversion reactions described above to obtain the liquid product, may be contained in a DHA reactor that is used in a DHA reaction stage. Such a DHA reaction stage, more generally, may comprise one or more DHA reactors containing such catalyst and may further comprise associated, auxiliary equipment (e.g., sensors, valves, gauges, control systems, etc.). In some embodiments, and preferably, only a single DHA reactor is needed for the DHA reaction stage. However, reactions associated with a DHA stage may also be carried out in more than one DHA reactor, for example two DHA reactors operating in parallel or in series.

A DHA reactor in the DHA reaction stage may contain a DHA catalyst comprising a catalytically active metal, or a compound of a catalytically active metal, suitable for catalyzing the dehydroaromatization of methane. The metal may be selected from the group consisting of lithium (Li), beryllium (Be), sodium (Na), magnesium (Mg), aluminum (Al), calcium (Ca), scandium (Sc), titanium (Ti), vanadium (V), chromium (Cr), manganese (Mn), iron (Fe), cobalt (Co), nickel (Ni), copper (Cu), rubidium (Rb), strontium (Sr), yttrium (Y), zirconium (Zr), niobium (Nb), molybdenum (Mo), ruthenium (Ru), rhodium (Rh), palladium (Pd), indium (In), antimony (Sb), barium (Ba), lanthanum (La), cerium (Ce), tantalum (Ta), tungsten (W), rhenium (Re), osmium (Os), iridium (Ir), platinum (Pt), lead (Pb), thorium (Th), and uranium (U), with a preferred metal being molybdenum (Mo). Combinations of these metals and/or metal compounds may also be used, such as a combination of cobalt (Co) and molybdenum (Mo). Normally, in view of presence of $H_2S$ in the methane-containing fresh feed or other feedstock to which the DHA catalyst is exposed, the active metal may be in its sulfided form, i.e., the DHA catalyst may comprise a metal sulfide compound of any one or more of these dehydroaromatization active metals. DHA catalysts of particular interest comprise one or more metal sulfide compounds of the formula $M_xS_y$, or one or more dehydroaromatization active metals M of such metal sulfide compound(s) (e.g., that form such metal sulfide compound(s) in the DHA reactor (in situ)), wherein x and y are integers that depend on the oxidation stage of M, and further wherein the metal sulfide compound has a melting temperature of greater than about 900° C., such as greater than about 1000° C. Preferred metals M may, therefore, be selected from the group consisting of Li, Be, Na, Mg, Al, Ca, Sc, Ti, V, Cr, Mn, Fe, Co, Cu, Rb, Sr, Y, Zr, Nb, Mo, Ru, Rh, In, Sb, Ba, La, Ce, Ta, W, Re, Os, Ir, Pb, Th, U, and combinations thereof. More preferred metals M may be selected from the group consisting of Li, Be, Na, Mg, Al, Ca, Ti, Cr, Mn, Fe, Co, Cu, Sr, Y, Nb, Mo, In, Sb, Ba, Ta, Pb, La, Ce, Th, and combinations thereof. Especially preferred metals M are Co, Mo, and a combination of Co and Mo. Specific metal sulfide compounds include $LiS_2$, BeS, $Na_2S$, MgS, $Al_2S_3$, CaS, TiS, CrS, $Cr_2S_3$, MnS, FeS, CoS, $Cu_2S$, SrS, $Y_2S_3$, $NbS_3$, $MoS_2$, $In_2S_3$, $Sb_2S_3$, BaS, $TaS_2$, PbS, $La_2S_3$, $Ce_2S_3$, and $ThS_2$.

The active metal(s), or compounds of these metals (e.g., metal sulfide compound(s)), may be supported on a suitable support material that is essentially refractory or inert in the conditions of the DHA reactor. Representative support materials include alumina, silica, titania, zirconia, ceria, and combinations thereof. A class of DHA catalysts may therefore comprise one or more metal sulfide compounds, such as one or more compounds of the formula $M_xS_y$ and meeting the criteria as described above (e.g., CoS and/or $MoS_2$), and a support material. Specific catalysts within this class include supported $MoS_2$ and supported sulfided CoMo. In representative DHA catalysts comprising a support, the active metal(s), whether or not present in the form of metal compound(s) such as metal sulfide compound(s), may be present in an amount, or combined amount, generally from about 1 wt-% to about 60 wt-%, typically from about 2 wt-% to about 40 wt-%, and often from about 3 wt-% to about 20 wt-%. In the case of such catalysts, the metal(s) M (e.g., Mo and/or Co), optionally in sulfided form, may be substantially the only metals present, such that any other metals, excluding metals, such as metal oxides, used in the support, may be present only in amounts of less than about 2% by weight or even less than about 1% by weight. Particular DHA catalysts comprise $MoS_2$ or sulfided CoMo on any of the support materials described above, including alumina-supported $MoS_2$ and alumina-supported sulfided CoMo. In the case of alumina-supported $MoS_2$, the catalyst may comprise a substantial proportion of $MoS_2$, such as greater than about 30 wt-% weight $MoS_2$ (e.g., from about 30 wt-% to about 85 wt-% $MoS_2$ or from about 50 wt-% to about 80 wt-% $MoS_2$). Alumina may be present in an amount from about 5 wt-% to about 35 wt-%, such as from about 10 wt-% to about 25 wt-%. In the case of alumina-supported sulfided CoMo, the catalyst may comprise Co in an amount from about 1 wt-% to about 15 wt-%, such as from about 2 wt-% to about 10 wt-%, and such catalyst may comprise Mo in an amount from about 3 wt-% to about 30 wt-%, such as from about 5 wt-% to about 20 wt-%. The balance of an alumina-supported sulfided CoMo catalyst (excluding the sulfur that is present) may be alumina. In the case of either alumina-supported $MoS_2$ or alumina-supported sulfided CoMo catalysts, support materials (e.g., metal oxides) other than alumina may be present in amounts of less than about 10 wt-%, less than about 5 wt-%, or even less than about 1 wt-%.

Suitable conditions in the DHA reaction stage, or in a DHA reactor that is used in this stage for carrying out the contacting of the methane-containing fresh feed or other feedstock with the DHA catalyst, may include a temperature generally from about 800° C. to about 1200° C., typically from about 900° C. to about 1000° C., and often from about 950° C. to about 1100° C. These conditions may also include a total absolute pressure generally from about 100 kPa to about 2.1 MPa, typically from about 100 kPa to about 1 MPa, and often from about 100 kPa to about 300 kPa. These conditions may further include a weight hourly space velocity (WHSV) generally from about 0.01 $hr^{-1}$ to about 5 $hr^{-1}$, typically from about 0.05 $hr^{-1}$ to about 1 $hr^{-1}$, and often from about 0.1 $hr^{-1}$ to about 0.5 $hr^{-1}$. As is understood in the art, the WHSV is the weight flow of a total feed (e.g. the feedstock comprising methane and $H_2S$) to a reactor, divided by the weight of the DHA catalyst in the reactor and represents the equivalent catalyst bed weights of the feedstock processed every hour. The WHSV is related to the inverse of the reactor residence time.

Performance Criteria, Product Quality

Using DHA catalysts under DHA conditions, as described above, a number of performance criteria associated with the DHA reactor or reaction stage may be realized. In the case of continuous operation, the various quantities, as described below for determining performance criteria, are obtained over a given time period at steady-state. Single-pass (once-through) $H_2S$ conversion can be determined on the basis of $H_2S_{in}$, representing the number of moles (or grams) of $H_2S$ that is fed (input) to the DHA reaction stage (e.g., the number of moles or grams of $H_2S$ in the feedstock comprising methane and $H_2S$, that is fed to a DHA reactor containing the DHA catalyst), and $H_2S_{out}$, representing the number of moles (or grams) of $H_2S$ that is withdrawn (output) from the DHA reaction stage (e.g., the number of moles or grams of $H_2S$ in the methane-containing gaseous product, that is withdrawn from a DHA reactor containing the DHA catalyst and assuming that $H_2S$ losses in the liquid product are negligible). Single-pass (once-through) $H_2S$ conversion can then be calculated as $1-H_2S_{out}/H_2S_{in}$, expressed as a percentage. In an analogous manner, single-pass (once-through) methane conversion can be determined on the basis of methane that is fed to the DHA reaction stage, in the feedstock comprising methane and $H_2S$, and withdrawn from the DHA reaction stage, in the methane-containing gaseous product.

In view of the fact that $H_2S$ is typically the limiting reactant in the soft oxidation reaction of methane and $H_2S$ as described above, single-pass $H_2S$ conversion may exceed single-pass methane conversion. However, it is also possible, considering the conversion of methane to aromatic hydrocarbons by DHA reactions, for single-pass methane conversion to exceed single-pass $H_2S$ conversion. Single-pass $H_2S$ conversion is generally from about 30% to about 95%, typically from about 40% to about 90%, and often from about 50% to about 85%. Advantageously, significant $H_2S$ conversion levels provide a methane-containing gaseous product having a substantially reduced $H_2S$ content. This can render the methane-containing gaseous product more easily treatable (e.g., using an $H_2S$ adsorbent) to achieve sufficiently low $H_2S$ level that allow further use of this product, such as by combustion to generate electricity. That is, the economics associated with treatment to obtain a product of a desired quality (e.g., a certain maximum $H_2S$ concentration) may be substantially improved. According to representative embodiments, the methane-containing gaseous product may have an $H_2S$ concentration of less than about 2 vol-%, less than about 1 vol-%, or even less than about 0.5 vol-%. Such $H_2S$ concentrations may be achieved, for example, in the case of feedstocks comprising methane and $H_2S$, with the $H_2S$ being present in concentrations of several volume percent (e.g., from about 3 vol-% to about 8 vol-% $H_2S$).

According to further embodiments of the invention, therefore, the methods (and apparatuses) described herein may comprise (or may be further configured for) treating, in a gas purification stage, the methane-containing gaseous product to further remove $H_2S$ (beyond the amount removed from conversion to organic sulfur compounds in the liquid product) to provide an $H_2S$-depleted methane product. This product may, for example, have an $H_2S$ concentration of less than about 1000 vol-ppm, less than 100 vol-ppm, or even less than about 10 vol-ppm, depending on the particular treatment for sulfur removal. For example, the methane-containing gaseous product may be contacted with a solid adsorbent, selective for $H_2S$ adsorption, to achieve such desired $H_2S$ concentrations in the $H_2S$-depleted methane product. According to other embodiments, the methane-containing gaseous product may be treated, in a gas purification stage, using pressure swing adsorption (PSA), including rapid cycle pressure swing adsorption (RCPSA), to provide the $H_2S$-depleted methane product having an $H_2S$ concentration as described above. In yet further embodiments, the methane-containing gaseous product may be treated, in a gas purification stage, using a membrane (e.g., one or more stages of membrane separation) to provide the $H_2S$-depleted methane product having an $H_2S$ concentration as described above. Examples of membranes include silicone membranes that may be formed as hollow fibers (microtubes) and arranged in a module with a surrounding housing or shell. PermSelect® silicone membranes, used in gas separation, provide more specific examples.

Single-pass methane conversion, via both soft oxidation and methane dehydroaromatization, is generally from about 20% to about 75%, typically from about 30% to about 65%, and often from about 35% to about 50%. Accordingly, unconverted methane generally represents a significant portion of the methane-containing gaseous product. For example, the methane-containing gaseous product may have a methane concentration generally from about 30 vol-% to about 80 vol-%, typically from about 35 vol-% to about 70 vol-%, and often from about 40 vol-% to about 65 vol-%. This concentration is dependent on the extent to which methane is converted to hydrogen via the soft oxidation reaction, with higher reaction temperatures leading directionally to higher hydrogen concentrations in the methane-containing gaseous product. Such hydrogen concentrations are generally from about 20 vol-% to about 70 vol-%, typically from about 25 vol-% to about 60 vol-%, and often from about 30 vol-% to about 50 vol-%. The presence of hydrogen in the methane-containing gaseous product, or otherwise in an $H_2S$-depleted methane product that is separated with a reduced concentration of $H_2S$, contributes to the combustive heating value of such products. In addition to methane, hydrogen, and $H_2S$, the balance of the methane-containing gaseous product may comprise predominantly or substantially all (e.g., greater than 95 vol-% of) ethylene, which was surprisingly was discovered to be, in many cases, a significant byproduct of the DHA reaction. Ethylene is valuable component of the DHA effluent from the DHA reaction stage (e.g., DHA reactor), having the potential for downstream conversion to additional liquid products, and/or otherwise being a valuable component of the methane-containing gaseous product. In representative embodiments, ethylene is present in this product, or otherwise in an $H_2S$-depleted methane product, depending on the method of its separation from the methane-containing gaseous product, at a concentration generally from about 1 vol-% to about 15 vol-%, typically from about 2 vol-% to about 12 vol-%, and often from about 3 vol-% to about 8 vol-%.

The single-pass (once-through) liquid product sulfur yield can be determined on the basis of $S_{in}$, representing the number of moles (or grams) of sulfur that is fed (input) to the DHA reaction stage (e.g., the number of moles or grams of sulfur in $H_2S$ in the feedstock comprising methane and $H_2S$, that is fed to a DHA reactor containing the DHA catalyst), and $LPS_{out}$, representing the number of moles (or grams) of sulfur that is withdrawn (output) from the DHA reactor in the liquid product (e.g., as disulfides, mercaptans, and/or thiophenes). Single-pass (once-through) liquid product sulfur yield can then be calculated as $LPS_{out}/S_{in}$, expressed as a percentage. The conversion of $H_2S$ to organic sulfur compounds effectively transforms the sulfur from a gaseous to a liquid state, allowing for it to be easily transported and economically converted to elemental sulfur, utilizing refinery-scale hydroprocessing, amine separation, and Claus process operations as described above. The non-sulfur containing components of the liquid product, and particularly the aromatic hydrocarbons, can then be used, following such hydroprocessing, as fuel (e.g., gasoline) blending components and/or specialty chemicals, such as precursors of petrochemical products (e.g., plastics). Single-pass liquid product sulfur yield is generally from about 20% to about 75%, typically from about 30% to about 70%, and often from about 40% to about 65%.

The single-pass (once-through) yields of the liquid product, or components of the liquid product, can be determined on the basis of $FEED_{in}$, representing the weight of the feedstock comprising methane and $H_2S$ that is fed (input) to the DHA reaction stage (e.g., DHA reactor), and the weight of the liquid product, or respective components of the liquid product, that are withdrawn (output) from the DHA reaction stage. If $LP_{out}$ represents the weight of the liquid product withdrawn (and/or recovered), and $AROM_{out}$, $BENZ_{out}$, $CS2_{out}$, and $THIOP_{out}$ represent the weight of aromatic hydrocarbons, benzene, carbon disulfide, and thiophene, respectively, in this liquid product withdrawn (and/or recovered), then the single-pass (once-through) liquid product yield can be calculated as $LP_{out}/FEED_{in}$, and the single-pass (once-through) yields of aromatic hydrocarbons, benzene, carbon disulfide, and thiophene, can be calculated as $AROM_{out}/FEED_{in}$, $BENZ_{out}/FEED_{in}$, $CS2_{out}/FEED_{in}$, and $THIOP_{out}/FEED_{in}$, respectively, expressed as percentages. In representative embodiments, the single-pass (once through) liquid product yield is generally from about 10% to about 35%, typically from about 12% to about 30%, and often from about 15% to about 25%. The single pass (once-through) aromatic hydrocarbon and benzene yields (in view of the predominant aromatic hydrocarbon being benzene in most cases) are, independently, generally from about 10% to about 35%, typically from about 12% to about 30%, and often from about 15% to about 25%. In some embodiments, however, aromatic hydrocarbon yields may be shifted toward naphthalene (e.g., under more severe operating conditions, such as higher DHA reaction temperatures), such that the single pass (once-through) benzene yields may be reduced, for example to generally from about 5% to about 25%, typically from about 6% to about 15%, and often from about 7% to about 12%. The single pass (once-through) carbon disulfide yield is generally from about 1% to about 15%, typically from about 2% to about 12%, and often from about 3% to about 8%. The single pass (once-through) thiophene yield is generally from about 0.5% to about 8%, typically from about 1% to about 6%, and often from about 1.5% to about 4%.

Optional Ethylene Oligomerization

Further aspects of the invention are associated with the discovery, as described above, of particular processes in which ethylene is produced as a byproduct of the DHA reaction and which may be present in the effluent of the DHA reaction stage (e.g., DHA reactor). According to one embodiment for exploiting this generation of ethylene, an ethylene oligomerization (EO) reaction stage is used downstream of the DHA reaction stage, in order to convert this ethylene to additional liquid hydrocarbons, and particularly aromatic hydrocarbons such as ethylbenzene. In this manner, the addition of an ethylene oligomerization reaction stage can increase the yields of liquid product and aromatic hydrocarbons (either once-through yields, or otherwise total yields in the case of recycle operation as described below) by about 1% to about 10%, such as from about 2% to about 7%, relative to a baseline operation in which all parameters are the same, with the exception of excluding the EO reaction stage. In view of the yields given above, therefore, the single-pass (once through) liquid product yield, using this additional reaction stage, may be generally from about 11% to about 45%, typically from about 13% to about 40%, and often from about 16% to about 35%. Likewise, the single-pass aromatic hydrocarbon yield, using this additional reaction stage, may be generally from about 11% to about 45%, typically from about 13% to about 40%, and often from about 16% to about 35%. Those skilled in the art will appreciate that even incremental increases in yields of liquid product can result in a substantial improvement in overall product value and process economics.

The EO catalyst, used to carry out conversion of at least a portion (e.g., the majority) of the ethylene in the effluent (output) of the DHA reaction stage, may be contained in an EO reactor that is used in an EO reaction stage. Such an EO reaction stage, more generally, may comprise one or more EO reactors containing such catalyst and may further comprise associated, auxiliary equipment (e.g., sensors, valves, gauges, control systems, etc.). In some embodiments, and preferably, only a single EO reactor is needed for the EO reaction stage. However, reactions associated with an EO reaction stage may also be carried out in more than one EO reactor, for example two EO reactors operating in parallel or in series.

An EO reactor in the optional EO reaction stage may contain an EO catalyst having strong acid sites. Acid sites may be determined, for example, by temperature programmed desorption (TPD) of a quantity of ammonia (ammonia TPD), from an ammonia-saturated sample of the catalyst, over a temperature from 275° C. to 500° C., which is beyond the temperature at which the ammonia is physisorbed. The quantity of acid sites, in units of milliequivalents of acid sites per gram (meq/g) of catalyst, therefore corresponds to the number of millimoles of ammonia that is desorbed per gram of catalyst in this temperature range. Representative solid catalysts are polymeric catalysts having strong acid sites (e.g., sulphonic acid sites), in an amount of at least about 1.5 meq/g (e.g., from about 1.5 to about 8 meq/g) of acid sites, or at least about 2.5 meq/g (e.g., from about 2.5 to about 5.5 meq/g) of acid sites. Particular catalysts are those strong acid catalysts within the group of Amberlyst™ Polymeric Catalysts and these include Amberlyst™ 15, Amberlyst™ 35, Amberlyst™ 36, Amberlyst™ 16, Amberlyst™ 31, Amberlyst™ 33, Amberlyst™ 121, Amberlyst™ 131, Amberlyst™ 70, Amberlyst™ 39, Amberlyst™ 46, Amberlyst™ CH10, Amberlyst™ CH28, and Amberlyst™ CH43, Other examples of polymeric catalysts having strong acid sites include Dowex® DR-2030.

Suitable conditions in the optional EO reaction stage, or in an EO reactor that is used in this stage for carrying out the contacting of at least a portion of the effluent (output) of the DHA reaction stage (e.g., DHA reactor), and thereby oligomerize ethylene contained in this effluent and produce aromatic hydrocarbons, may include a temperature generally from about 75° C. to about 400° C., typically from about 100° C. to 350° C., and often from about 150° C. to about 300° C. These conditions may also include a total absolute pressure within the ranges described above with respect to the DHA reaction stage, as described above. That is, according to preferred embodiments, no compression or substantial depressurization of the DHA effluent is required, upstream of the optional EO reaction stage. A nominal pressure drop, for example in the range of about 5 kPa to about 70 kPa, associated with losses in the equipment between the DHA reaction stage (e.g., DHA reactor) and EO reaction stage (e.g., EO reactor), such as piping and possibly a cooler, is expected. Accordingly, representative pressures in the EO reaction stage (e.g., EO reactor) are from about 100 kPa to about 2.1 MPa, typically from about 100 kPa to about 1 MPa, and often from about 100 kPa to about 295 kPa. The weight hourly space velocity (WHSV) in the EO reaction stage (e.g., EO reactor) is generally from about 0.01 $hr^{-1}$ to about 10 $hr^{-1}$, typically from about 0.05 $hr^{-1}$ to about 5 $hr^{-1}$, and often from about 0.1 $hr^{-1}$ to about 1 $hr^{-1}$, defined in an analogous manner as described above with respect to WHSV in the DHA reaction stage.

Once-Through and Optional Recycle Operation

The processes (and apparatuses) described herein may be carried out with (or configured for) once-through operation, whereby the feedstock comprising methane and $H_2S$ is input and the separated liquid product and methane-containing gaseous product, optionally with treating to further reduce its $H_2S$ concentration, are withdrawn. In the case of once-through operation, the "methane-containing fresh feed" and the "feedstock comprising methane and $H_2S$" are equivalent, and the "single-pass" performance criteria described above (single-pass conversion levels and yields) are the same as the performance criteria of the overall process. As described above, according to further embodiments of the invention, the methods (and apparatuses) described herein may comprise (or may be further configured for), in a gas purification stage, treating the methane-containing gaseous product to further remove $H_2S$ (beyond the amount removed from conversion to organic sulfur compounds in the liquid product) to provide an $H_2S$-depleted methane product. Such treating can also provide a separated gas (e.g., PSA tail gas or membrane retentate gas) that is enriched in $H_2S$, relative to the $H_2S$-depleted methane product and methane-containing gaseous product. A sour gas PSA, for example, can provide an $H_2S$-depleted methane product having a concentration of $H_2S$ of less than about 10 vol-ppm (e.g., from about 0.1 vol-ppm to less than about 10 vol-ppm). The recovery of $H_2S$ in the separated gas, removed from this $H_2S$-depleted methane product, may be greater than about 80% (e.g., from about 80% to about 99%), or even greater than about 90% (e.g., from about 90% to about 99%). For a given PSA adsorbent, or a given membrane, the degree of $H_2S$ removal from the hydrogen product and degree of recovery of $H_2S$ in the separated gas can be varied by manipulating operating parameters, such as the number of separation stages.

The separations described above for providing an H$_2$S-depleted methane product, including PSA (e.g., RCPSA) and membrane separation (e.g., using a module containing a PermSelect® silicone membrane), according to particular embodiments comprising treating the methane-containing gaseous product to remove H$_2$S, can provide a separated gas stream with various compositions, depending on the particular separation used in a gas purification stage. According to further embodiments of the invention, representative processes further comprise (and representative apparatuses are further configured for) separating, in a gas purification stage, all or a portion of the methane-containing gaseous product to provide the H$_2$S-depleted methane product and recycling all or a portion of the separated gas, from this product, as a methane-containing gaseous recycle. Such recycle operation can beneficially increase the "single-pass" performance criteria described above (single-pass conversion levels and yields), higher overall performance criteria (overall conversion levels and yields). In the case of recycle operation, the "feedstock comprising methane and H$_2$S," and introduced to the DHA reaction stage (e.g., DHA reactor), may be a combined feedstock, resulting from the combination of the "methane-containing fresh feed," as described above, and the methane-containing gaseous recycle, obtained from the separation of the H$_2$S-depleted methane product. In this case, the "methane-containing fresh feed" and the "feedstock comprising methane and H$_2$S" are not equivalent, and overall performance criteria (as opposed to the single-pass performance) may be determined in an analogous manner as described above, but in this case on the basis of the "methane-containing fresh feed" that is input to the process (as opposed to the "feedstock comprising methane and H$_2$S") and on the basis of the "H$_2$S-depleted methane product" that is withdrawn from the process (as opposed to the "methane-containing gaseous product").

In the case of recycle operation, the single-pass performance criteria (single-pass conversion levels and yields) may be in the ranges as described above. The higher overall performance criteria may depend, at least in part, on the particular separation of the methane-containing gaseous product to provide the H$_2$S-depleted methane product and the methane-containing gaseous recycle. Using PSA separation or membrane separation in a gas purification stage, a substantial proportion of the hydrogen present in the methane-containing gaseous product may be separated into the H$_2$S-depleted methane product, such that this product may have a hydrogen concentration of greater than about 60 vol-% (e.g., from about 60 vol-% to about 99 vol-%), such as greater than about 70 vol-% (e.g., from about 70 vol-% to about 90 vol-%). This product may have a methane concentration of less than about 40 vol-% (e.g., from about 10 vol-% to about 40 vol-%), such as less than about 30 vol-% (e.g., from about 15 vol-% to about 30 vol-%). As described above, the H$_2$S in the H$_2$S-depleted methane product may have a concentration of less than 1000 vol-ppm, such that further treatment (e.g., using an adsorbent) to obtain H$_2$S levels suitable for electricity generation generally become economical. PSA separation or membrane separation may, however, achieve much lower H$_2$S concentrations, for example, less than about 100 vol-ppm, or even less that about 10 vol-ppm, in the H$_2$S-depleted methane product.

Other types of PSA separation or membrane separation in a gas purification stage, depending on the particular PSA adsorbent or membrane used, may separate a greater proportion of methane present in the methane-containing gaseous product into the H$_2$S-depleted methane product, such that this product may have a methane concentration from about 50 vol-% to about 85 vol-%, for example from about 60 vol-% to about 75 vol-%. This product may have a hydrogen concentration from about 10 vol-% to about 45 vol-%, for example from about 20 vol-% to about 35 vol-%. Despite differences in the proportion of methane (and possibly other hydrocarbons) in the methane-containing gaseous product that can be separated into the H$_2$S-depleted methane product using different separations, an H$_2$S-depleted methane product can nonetheless be provided with low H$_2$S concentrations in the ranges given above. In the case of separation of a higher proportion of methane into this product, higher proportions of other larger-molecule products are generally also present. Therefore, particular embodiments may further comprise separating a condensed liquid product from (e.g., by cooling of) the H$_2$S-depleted methane product. This condensed liquid product may contain additional, condensed amounts of aromatic hydrocarbons and organic sulfur compounds that can increase the yield of liquid product overall, as well as the yield of these valuable liquid components.

As can be appreciated by those skilled in the art, recycling of greater proportions of H$_2$S and methane, in the methane-containing gaseous recycle, back to the DHA reaction stage (e.g., DHA reactor), can directionally result in higher overall H$_2$S conversion and overall methane conversion. In the case of recycle operation, the overall H$_2$S conversion may be from about 50% to about 99%, such as from about 70% to about 95%. Overall methane conversion, via both soft oxidation and methane dehydroaromatization, may be from about 50% to about 95%, such as from about 65% to about 90%. As can be further appreciated, recycle operation can also result in higher overall product yields, relative to the corresponding single-pass product yields. For example, overall total liquid product yield may be from about 25% to about 65%, such as from about 30% to about 50%. Overall liquid product sulfur yield may be from about 50% to about 90%, such as from about 60% to about 70%. Overall aromatic hydrocarbon and benzene yields (in view of the predominant aromatic hydrocarbon being benzene in most cases) may be from about 25% to about 50%, such as from about 30% to about 45%. In some embodiments, however, aromatic hydrocarbon yields may be shifted toward naphthalene (e.g., under more severe operating conditions, such as higher DHA reaction temperatures), such that the overall benzene yields may be reduced, for example to a range from about 5% to about 25%, such as from about 10% to about 20%. Overall carbon disulfide yield may be from about 3% to about 25%, such as from about 5% to about 20%. Overall thiophene yield may be from about 1% to about 10%, such as from about 2% to about 8%.

Heat Integration and Reactor/Furnace Construction

Processes as described herein advantageously convert a sour methane-containing feedstock, having a relatively high H$_2$S concentration, to provide a sweetened methane-containing gaseous product, having a relatively low H$_2$S concentration. Both the feedstock and product, by virtue of the presence of methane and/or other combustible (flammable) gases, have heating value. The methane-containing gaseous product and, in the case of recycle operation, the H$_2$S-depleted methane product separated therefrom, may additionally contain a significant concentration of hydrogen, contributing to the heating value of these products. The heating value of any feedstock or product stream may be useful for generating at least a portion of the heating requirement for the DHA reactor, which generally operates at elevated temperatures (e.g., greater than about 500° C.) and more typically at those temperatures described above as being suitable for this reactor. According to particular embodiments, the DHA reactor may be disposed in a furnace, which may optionally utilize, as fuel, any suitable process stream, such a supplemental supply of the methane-containing fresh feed or the methane-containing feedstock, or otherwise a portion of the methane-containing gaseous product or a portion of the $H_2S$-depleted methane product. Advantageously, in the case of utilizing the product streams as fuel, the reduced concentration of $H_2S$ relative to the fresh feed or feedstock can lead to important advantages associated with a reduced severity (e.g., corrosivity) of operation of the furnace. Such advantages are particularly relevant in view of the high DHA reactor operating temperatures that require special considerations in terms of construction materials for both the reactor and furnace. These materials must be not only temperature resistant, but also resistant to corrosion when exposed to gases containing $H_2S$ and other sulfur-bearing species at these high operating temperatures.

With respect to the DHA reactor, as the environment within this reactor includes both high temperatures and potentially high $H_2S$ concentrations (e.g., concentrations as described above with respect to the methane-containing fresh feed or methane-containing feedstock), protection of the interior surfaces of this reactor may be warranted. For example, the DHA reactor may comprise an inner liner or "sleeve" of a different material, or a coating of a different material, relative to the material of an outer shell that may surround, e.g., completely enclose, the inner liner. The inner liner may, in turn, be exposed to the contents of the DHA reactor and also enclose a bed of DHA catalyst. The inner liner may be constructed of a material that is suitably inert to (or corrosion resistant in) the DHA reaction environment, with alumina, quartz, glass, ceramic, and molybdenum being representative of materials having this property as well as the ability to provide sufficient heat transfer to the outer shell. In this case, the outer shell, being protected from corrosion due to the inner liner, may be constructed of a variety of materials, including carbon or stainless steel (e.g., ASME grades 303, 304, or 316). Optionally, the outer shell may be constructed of corrosion-resistant nickel alloy, for example having a Ni content of at least about 72 wt-%, such as Alloy 600 (e.g., Inconel® 600). Whereas such high-Ni content alloys are generally not sufficiently corrosion resistant under typical DHA reaction conditions of high temperature, significant $H_2S$ concentration, and an overall reducing environment, the inner liner may offer sufficient corrosion protection to enable the use of these alloys. If an inner liner is used, the environment between the inner liner and outer shell may be regulated, for example, by flowing a purge gas though the space between the liner and shell. According to specific embodiments, an inert gas such as nitrogen, argon, or helium may be used to purge this space. By using such inert gas, an undesirable environment exterior to the inner liner and interior to the outer shell, such as an oxidizing environment, may be effectively avoided.

In cases in which an inner liner is absent, the interior surface of the outer shell (or reactor interior surface) is directly exposed to, and must be able to withstand, the DHA reaction environment. In this case, corrosion-resistant materials based on Iron-Chromium-Aluminum (FeCrAl) alloys may be preferred. Such alloys may be oxidized in order to ensure that the reactor interior surface (wall) is protected by a thick layer of aluminum oxide prior to use. As a result of oxidation, these alloys may be made highly resistant to corrosion in high-temperature, high-sulfur environments. A particular example of an FeCrAl alloy is commercially available under the trade name Kanthal (20.5 wt-% Cr, 5.8 wt-% Al, balance Fe).

With respect to the furnace in which the DHA reactor is disposed, construction materials of the furnace shell and/or burners will often depend on the nature of the fuel being combusted in this furnace, with potential candidate sources of such fuel being process streams as described above. In the case of the furnace fuel comprising a supplemental supply of the methane-containing fresh feed or the methane-containing feedstock, the furnace fuel may be considered a "high-sulfur fuel," and the concentration of $H_2S$ in the interior of the furnace, as well as the interior of the DHA reactor, may be relatively high, such as in a range described above with respect to these process streams. In this case, the furnace interior surface (as well as the reactor interior surface) must be corrosion resistant upon exposure to potentially high $H_2S$ concentrations at the DHA reaction temperature. If a corrosion-resistant inner liner or coating is used in the furnace, then the furnace may be constructed of a material as described above with respect to the DHA reactor in the case of using such liner or coating, for example an alloy such as carbon or stainless steel, or a more corrosion-resistant nickel alloy. If such corrosion-resistant liner or coating is absent in the furnace, then the furnace may be constructed of a more corrosion resistant alloy such as an FeCrAl alloy described above, and preferably oxidized prior to use. Super-alloys such as Haynes HR-160 (37 wt-% Ni, 29 wt-% Co, 28 wt-% Cr, 2 wt-% Fe, 1 wt-% Mo, 2.75 wt-% Si, 1 wt-% W, 0.5 wt-% Mn, 0.5 wt-% Ti, 0.5 wt-% C) may also be used.

In the case of the furnace fuel comprising a portion of the methane-containing gaseous product, and/or a portion of the $H_2S$-depleted methane product, the furnace fuel may be considered a "low-sulfur fuel," and the concentration of $H_2S$ in the interior of the furnace may be well below that in the interior of the DHA reactor, such as in a range described above with respect to the methane-containing gaseous product or the $H_2S$-depleted methane product. Both the furnace and the reactor exterior surface (wall) may be constructed of alloy such as carbon or stainless steel, or a corrosion-resistant nickel alloy, as described above. A specific low-sulfur fuel may comprise, for example, at least a portion of an $H_2S$-depleted methane product that is obtained from the treatment of the methane-containing gaseous product by RCPSA to remove $H_2S$, which is predominantly recovered (e.g., recovered in an amount of at least 80%) in a separated gas, which may be a methane-containing gaseous recycle as described herein. In the case of RCPSA separation, or PSA separation generally, the low-sulfur fuel or portion of the $H_2S$-depleted methane product may comprise predominantly hydrogen (e.g., at least about 80 vol-% $H_2$) that is generated in the DHA reactor and purified by the PSA separation. RCPSA may therefore be used for separation of a methane-containing gaseous product into both (i) an $H_2S$-depleted methane product, suitable for combustion to generate at least a portion of the heat required for the DHA reaction stage, and (ii) a methane-containing gaseous recycle. In a specific example, (A) the methane-containing gaseous product, or feed to the RCPSA, may have the following composition: $H_2$—26.0 vol-%; $CH_4$—67.0 vol-%; $C_2H_6$—2 vol-%; $C_2H_4$—4 vol-%, $H_2S$—1 vol-%, (B) the $H_2S$ depleted methane product, all or a portion of which may be used as a low-sulfur fuel for the furnace, may have the following composition: $H_2$—90.0 vol-%; $CH_4$—9.9 vol-%; $C_2H_6$—0.1 vol-%, and (C) the methane-containing gaseous recycle may have the following composition $H_2$—6.1 vol-%; $CH_4$—84.7 vol-%; $C_2H_6$—2.6 vol-%; $C_2H_4$—5.2 vol-%, $H_2S$—1.3 vol-%.

According to a specific embodiment, the DHA reactor may comprise a corrosion-resistant inner sleeve, which prevents the reactor interior surface (wall) from being exposed to $H_2S$, and the DHA reactor may be disposed in a furnace that combusts low-sulfur fuel for heat generation. In this case, the outer shell of the DHA reactor and the furnace may advantageously be constructed of any of the alloys described above. In another specific embodiment, the inner sleeve in the DHA reactor may be omitted. In this case, the reactor may be constructed of a material that is capable of withstanding both high temperatures and high sulfur concentrations, such as an FeCrAl alloy. The furnace shell and burner components, however, may be constructed of a material such as Alloy 600, which is capable of tolerating the conditions in the furnace, but is not uniquely resistant to sulfur corrosion.

Representative Embodiment

Figure 2:
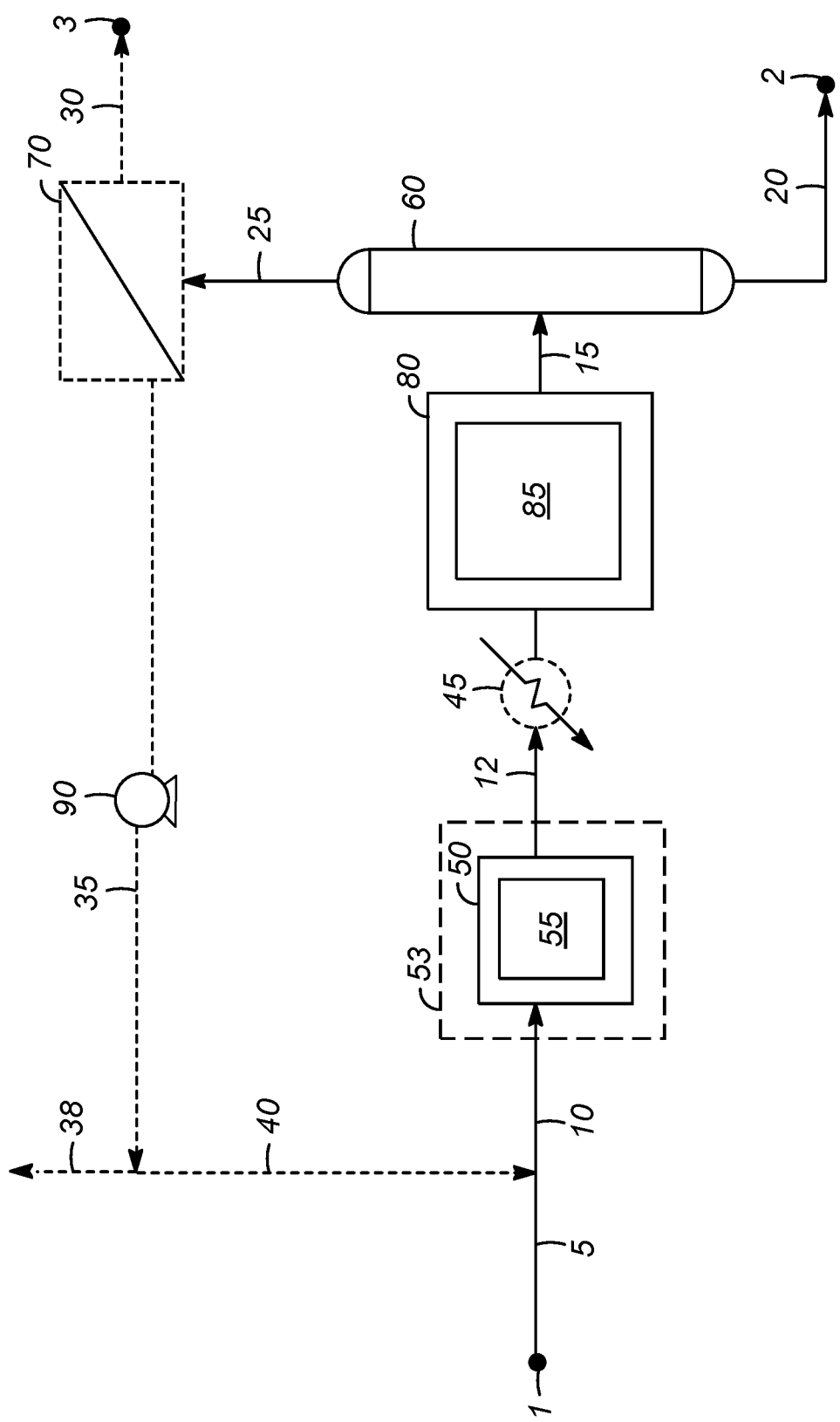
FIG. 2 depicts flowscheme that illustrates a representative process as described herein, comprising a methane DHA reaction stage and downstream ethylene oligomerization (EO) reaction stage to improve liquid hydrocarbon yields.

FIGS. 1 and 2 illustrate representative processes in which a feedstock comprising methane and $H_2S$ 10 is fed or input to DHA reaction stage (e.g., DHA reactor) 50 to recover liquid product 20 comprising one or more aromatic hydrocarbons and one or more organic sulfur compounds. Any of the conditions, catalysts, performance criteria, and product quality aspects, as well as recycle operation aspects, as described above are applicable to these representative processes. DHA reaction stage 50 comprises DHA catalyst 55, used to convert methane and $H_2S$ in feedstock 10 by soft oxidation and dehydroaromatization. DHA effluent 12, withdrawn from DHA reaction stage 50, is fed to separator 60 that performs the separation of liquid product 20 from methane-containing gaseous product 25. As shown in FIG. 1, optional effluent cooler 45 may be used to provide the DHA effluent to separator 60 as cooled DHA effluent 15. In general, some or all of DHA effluent 12 can be fed to separator 60, optionally following this cooling in effluent cooler 45, and/or optionally following one or more other intervening operations such as pressurizing, depressurizing, separation of one or more components (e.g., removal of condensed water), addition of one or more components (e.g., addition of a portion of the methane-containing gaseous recycle), and/or reaction of one or more components (e.g., reaction of ethylene to produce aromatic hydrocarbons). In the embodiment of FIG. 2, for example, intervening operations of both cooling in optional effluent cooler 45 and reaction of ethylene in EO reaction stage (e.g., EO reactor) 80 containing EO catalyst 85, are illustrated. In this embodiment, therefore, cooled DHA effluent 15 of FIG. 1 is replaced by cooled EO effluent 15 that is withdrawn from EO reaction stage 80 and fed to separator 60. Also in this embodiment, DHA effluent 12, withdrawn from DHA reactor 50, is fed to EO reaction stage (e.g., EO reactor) 80.

As illustrated in FIGS. 1 and 2, methane-containing gaseous product 25, or at least a portion of this product, may be fed to optional gas purification stage 70 to provide $H_2S$-depleted methane product 30 and methane-containing gaseous recycle 35, as described above. All or a portion 40 of methane-containing gaseous recycle 35 may then be combined, for example using compressor 90 to increase its pressure to that used in DHA reaction stage 50, with methane-containing fresh feed 5. This feed may be any feedstock as described above, and it may therefore represent a net input to the overall process, whereas the combination of methane-containing fresh feed 5 and methane-containing gaseous recycle 35 may provide a combined feed to DHA reaction stage as the feedstock comprising methane and $H_2S$. Optionally, to prevent an excessive accumulation of impurities (e.g., $CO_2$) and/or otherwise improve control of the composition of methane-containing gaseous recycle 35, recycle purge 38 may be used to vent or bleed a portion (e.g., less than about 10%, or less than about 5%) of methane-containing gaseous recycle 35.

In view of the generally high temperatures as described above that are suitable in DHA reaction stage 50, an optional furnace 53 may be used for heating this reaction stage. For example a DHA reactor may be disposed within furnace 53, which may be, for example, an electric furnace or a gas furnace. In either case, at least a portion of the heating requirement of furnace 53, and consequently at least a portion of the heating requirement of DHA reaction stage 50, may be generated from the combustion of available fuel, including any of those process streams depicted in FIGS. 1 and 2 having heating value. Examples of such available fuel include a supplemental supply of methane-containing fresh feed 5, a portion of methane-containing gaseous product 25, and/or a portion of $H_2S$-depleted methane product 30. In the case of these latter product streams, the lower concentration of $H_2S$ relative to methane-containing fresh feed 5 may have important implications in terms of reducing severity (e.g., corrosivity) of the environment of furnace 53, thereby permitting the use of lower-cost alloys as construction materials, such as those alloys as described above. In the case of an electric furnace, combustion of available fuel may be used for electricity generation (e.g., for generating at least a portion of the electricity requirement of this furnace and consequently indirectly generating at least a portion of its heating requirement). The advantages of combusting, for this purpose, methane-containing gaseous product 25, and/or a portion of $H_2S$-depleted methane product 30, in terms of the low concentration of $H_2S$ in these product streams, are described above. In the case of a gas furnace, combustion of available fuel, fed to this furnace, may directly generate at least a portion of the heating requirement of this furnace, as needed to carry out DHA reaction stage 50.

Aspects of the invention also relate to systems or apparatuses for performing processes as described herein, such as those depicted in FIGS. 1 and 2. The systems or apparatuses may comprise one or more of the following: (i) a dehydroaromatization (DHA) reactor 50 configured to connect, via a system input 1, to a source of methane-containing fresh feed 5 (which may be equivalent to a source of feedstock comprising methane and $H_2S$ 10 in the case of once-through operation), including any of the feedstocks described above. DHA reactor 50 may contain a DHA catalyst 55 as described above, may be disposed within optional furnace 53, and/or may be further configured to produce or provide, from feedstock comprising methane and $H_2S$ 10, DHA effluent 12, for example under DHA conditions as described above; (ii) an optional DHA effluent cooler 45 configured to receive (and/or cool) DHA effluent 12 from DHA reactor 50. DHA effluent cooler 45 may be connected to DHA reactor 50, or may otherwise have an inlet configured for connection to an outlet of this reactor; (iii) separator 60 configured to receive DHA effluent 12, or optionally cooled DHA effluent 15, from DHA reactor 50 and further configured to provide or separate, via system liquid outlet 2, liquid product 20. Separator 60 is further configured to provide or separate methane-containing gaseous product 25. According to the embodiment in FIG. 2, intermediate EO reactor 80, which may contain EO catalyst 85, may be configured to receive DHA effluent 12, or optionally cooled DHA effluent 15, from DHA reactor 50. Separator 60 may be connected to, or may have an inlet configured for connection to, an outlet of DHA reactor 50, or optionally an outlet of DHA effluent cooler 45, or optionally an outlet of EO reactor 80 (FIG. 2). Representative systems or apparatuses may further comprise gas purification stage 70 configured to receive methane-containing gaseous product 25 and further configured to provide, via system gas outlet 3, $H_2S$-depleted methane product 30. Gas purification stage 70 may be connected to separator 60 or may have inlet configured for connection to an outlet of separator 60. Gas purification stage 70 may be further configured to provide methane-containing gaseous recycle 35, and optionally configured to combine methane-containing gaseous recycle 35 with methane-containing fresh feed 5. Gas purification stage 70 may therefore be configured to provide feedstock comprising methane and $H_2S$ 10 to DHA reactor 50, as a combination of methane-containing fresh feed 5 and methane-containing gaseous recycle 35. Gas purification stage 70 may be connected to both separator 60 and DHA reactor 50, or may have an inlet configured for connection to an outlet of separator 60 and/or may include system gas outlet 3 and a second outlet configured for connection to an inlet of DHA reactor 50.

Advantageously, the simplicity of such systems and apparatuses allows for their operation on a small scale, such that they may be transportable in some embodiments, for example by truck, ship, train, or airplane, to a site of a suitable feedstock (e.g., a wellhead or source of stranded natural gas). The systems and apparatuses, or components thereof, may be mounted on a skid to facilitate their transport.

The following examples are set forth as representative of the present invention. These examples are not to be construed as limiting the scope of the invention as other equivalent embodiments will be apparent in view of the present disclosure and appended claims.

EXAMPLE 1

Pilot plant scale experiments were performed, in order to investigate the conversion of sour natural gas feedstocks directly to liquid and gaseous products, separated from the effluent of a methane DHA reactor. The compositions of these model feedstocks are shown in Table 1.

TABLE 1

Model Sour Natural Gas Feedstocks

| Component, vol-% | FEED #1 "Dry" | FEED #2 "Wet" | FEED #3 "Low $CO_2$" | FEED #4 "High $CO_2$" | FEED #5 "Low $H_2S$" |
|---|---|---|---|---|---|
| $CH_4$ | 95.0 | 70.0 | 65.6 | 61.8 | 73.0 |
| $C_2H_6$ | 0 | 20.0 | 18.8 | 17.6 | 20.0 |
| $C_3H_8$ | 0 | 5.0 | 4.7 | 4.4 | 5.0 |

TABLE 1-continued

Model Sour Natural Gas Feedstocks

| Component, vol-% | FEED #1 "Dry" | FEED #2 "Wet" | FEED #3 "Low $CO_2$" | FEED #4 "High $CO_2$" | FEED #5 "Low $H_2S$" |
|---|---|---|---|---|---|
| $H_2S$ | 5.0 | 5.0 | 4.7 | 4.4 | 2.0 |
| $CO_2$ | 0 | 0 | 6.2 | 11.8 | 0 |

From an initial screening of various possible catalyst types for their activity to catalyze soft oxidation and dehydroaromatization, a catalyst comprising sulfided CoMo on an alumina support was found to exhibit stable activity over a 7-day testing period with reproducible results. No increase in pressure drop across the catalyst bed was observed, indicative of the absence of any appreciable coking that would otherwise initiate plugging of the catalyst bed. This catalyst, as well as a supported $MoS_2$ catalyst that also demonstrated good performance, were selected for further evaluation of reaction conditions. For each observation, the given set of conditions was established for at least 4 hours, to ensure that the corresponding data (sample) acquisition and analysis was performed at steady-state. Table 2 provides a summary of the vol-% $H_2S$ measured in the gaseous product, as well as the wt-% of total liquid and various components recovered from the DHA reactor effluent, on the basis of the feed weight. These components, shown in Table 2, are namely ethylene, aromatic hydrocarbons (based on a fraction of $C_6^+$ hydrocarbons in the liquid product), carbon disulfide, and thiophene. Also shown is the combined wt-% of ethylene and total liquid product. These measurements were taken at 8 different reaction (reactor or catalyst bed) temperatures, as indicated in Table 2, during tests with FEED #2 according to Table 1 and containing 5 vol-% $H_2S$. Other conditions used to obtain the data in Table 2 included a reactor pressure of 150 kPa and a WHSV of 0.24 $hr^{-1}$, with the sulfided CoMo catalyst.

TABLE 2

Product Comp. & Yield Data, FEED #2, 150 kPa, 0.24 $hr^{-1}$ WHSV, sulfided CoMo

| Test | 1 | 2 | 3 | 4 | 5 | 6 | 7 | 8 |
|---|---|---|---|---|---|---|---|---|
| Reactor/Catalyst Temp, °C. | 482 | 760 | 816 | 871 | 927 | 981 | 1038 | 1069 |
| Gas, vol-% $H_2S$ | 3.12 | 2.65 | 2.79 | 2.37 | 1.67 | 1.38 | 1.54 | 1.65 |
| Product, wt-% total liquid | 0.04 | 0.19 | 1.49 | 8.64 | 14.38 | 17.56 | 15.19 | 15.77 |
| Product, wt-% ethylene | 0.03 | 3.4 | 11.3 | 17.2 | 9.9 | 4.8 | 3.4 | 2.2 |
| Product, wt-% aromatic HCBNs | 0.02 | 0.08 | 0.84 | 6.63 | 10.66 | 11.66 | 10.35 | 6.64 |
| Product, wt-% carbon disulfide | 0 | 0.01 | 0.34 | 2.22 | 4.21 | 4.63 | 4.34 | 2.82 |
| Product, wt-% thiophene | 0.01 | 0.1 | 0.37 | 0.99 | 1.65 | 2.20 | 0.34 | 0.15 |
| Product, wt-% liquid + ethylene | 0.07 | 3.6 | 12.9 | 27.0 | 26.4 | 23.2 | 18.4 | 11.8 |

The data in Table 3 were obtained during tests with FEED #1, including a reactor pressure of 150 kPa and a WHSV of 0.2 $hr^{-1}$, operating with the sulfided CoMo catalyst.

TABLE 3

Product Comp. & Yield Data, FEED #1, 150 kPa, 0.2 $hr^{-1}$ WHSV, sulfided CoMo

| Test | 1 | 2 | 3 | 4 |
|---|---|---|---|---|
| Reactor/Catalyst Temp, °C. | 871 | 982 | 1038 | 1066 |
| Gas, vol-% $H_2S$ | 3.91 | 2.54 | 1.59 | 1.65 |
| Product, wt-% total liquid | 0.84 | 6.62 | 13.88 | 8.64 |
| Product, wt-% ethylene | 0.03 | 3.4 | 11.3 | 14.76 |

TABLE 3-continued

Product Comp. & Yield Data, FEED #1, 150 kPa, 0.2 hr$^{-1}$ WHSV, sulfided CoMo

| Test | 1 | 2 | 3 | 4 |
|---|---|---|---|---|
| Product, wt-% aromatic HCBNs | 0 | 1.58 | 6.00 | 7.70 |
| Product, wt-% carbon disulfide | 0.83 | 4.60 | 7.05 | 6.49 |
| Product, wt-% thiophene | 0.01 | 0.44 | 0.83 | 0.57 |
| Product, wt-% liquid + ethylene | 1.5 | 9.2 | 18.3 | 19.2 |

The data in Table 4 were obtained during tests with FEED #3 and FEED #4, both containing $CO_2$. Test conditions included a reactor pressure of 150 kPa and a WHSV of 0.2 hr$^{-1}$, with the sulfided CoMo catalyst. The yield data in this table includes a calculation of the total liquid yield, based on the feed weight but excluding the $CO_2$ ($CO_2$-free basis).

TABLE 4

Product Comp. & Yield Data, FEED #3, 150 kPa, 0.2 hr$^{-1}$ WHSV, sulfided CoMo

| Test | 1 | 2 | 3 |
|---|---|---|---|
| Feedstock from Table 1 | FEED #3 | FEED #4 | FEED #4 |
| Reactor/Catalyst Temp, ° C. | 871 | 982 | 1038 |
| Gas, vol-% H$_2$S | 2.48 | 1.12 | 0.19 |
| Product, wt-% total liquid | 6.17 | 13.46 | 11.36 |
| wt-% total liquid (CO$_2$-free basis) | 6.63 | 15.19 | 12.93 |
| Product, wt-% ethylene | 20.35 | 6.55 | 3.66 |
| Product, wt-% aromatic HCBNs | 4.1 | 9.08 | 8.73 |
| Product, wt-% carbon disulfide | 1.4 | 3.42 | 2.04 |
| Product, wt-% thiophene | 0.87 | 0.98 | 0.59 |
| Product, wt-% liquid + ethylene | 26.5 | 20.0 | 15.0 |

The data in Table 5 were obtained during tests with FEED #5, including a reactor pressure of 150 kPa and operating with the sulfided CoMo catalyst. For these tests, the effect of varying both WHSV and reactor temperature were studied.

TABLE 5

Product Comp. & Yield Data, FEED #5, 150 kPa, sulfided CoMo

| Test | 1 | 2 | 3 | 4 | 5 | 6 | 7 |
|---|---|---|---|---|---|---|---|
| Reactor/Catalyst Temp, ° C. | 871 | 982 | 982 | 982 | 1038 | 1038 | 1038 |
| WHSV, hr$^{-1}$ | 0.17 | 0.17 | 0.08 | 0.34 | 0.17 | 0.08 | 0.34 |
| Gas, vol-% H$_2$S | 0.93 | 0.8 | 0.79 | 0.69 | 0.69 | 0.75 | 0.47 |
| Product, wt-% total liquid | 7.95 | 14.03 | 14.78 | 14.27 | 12.30 | 18.27 | 13.81 |
| Product, wt-% ethylene | 21.2 | 5.34 | 4.21 | 9.23 | 3.25 | 4.94 | 5.90 |
| Product, wt-% aromatic HCBNs | 6.10 | 12.06 | 13.17 | 12.61 | 10.55 | 16.93 | 12.41 |
| Product, wt-% carbon disulfide | 1.35 | 1.41 | 1.19 | 1.01 | 0.98 | 0.99 | 0.91 |
| Product, wt-% thiophene | 0.49 | 0.55 | 0.42 | 0.65 | 0.76 | 0.34 | 0.49 |
| Product, wt-% liquid + ethylene | 29.2 | 19.4 | 19.0 | 23.5 | 15.6 | 23.2 | 19.7 |

The data in Table 6 were obtained during tests with FEED #2, including a reactor pressure of 150 kPa and a WHSV of 0.14 hr$^{-1}$, operating with the supported MoS$_2$ catalyst.

TABLE 6

Product Comp. & Yield Data, FEED #2, 150 kPa, 0.14 hr$^{-1}$ WHSV, supported MoS$_2$

| Test | 1 | 2 | 3 | 4 | 5 |
|---|---|---|---|---|---|
| Reactor/Catalyst Temp, ° C. | 871 | 982 | 1038 | 1056 | 1093 |
| Gas, vol-% H$_2$S | 2.73 | 1.65 | 1.96 | 1.73 | 1.76 |
| Product, wt-% total liquid | 9.17 | 17.00 | 13.00 | 16.00 | 12.86 |
| Product, wt-% ethylene | 17.85 | 5.45 | 2.50 | 3.47 | 1.61 |
| Product, wt-% aromatic HCBNs | 6.96 | 12.07 | 10.50 | 12.00 | 10.51 |
| Product, wt-% carbon disulfide | 1.56 | 4.03 | 2.15 | 3.60 | 2.09 |
| Product, wt-% thiophene | 0.65 | 0.90 | 0.42 | 0.38 | 0.27 |
| Product, wt-% liquid + ethylene | 27.0 | 22.5 | 15.5 | 19.5 | 14.5 |

Figure 3:
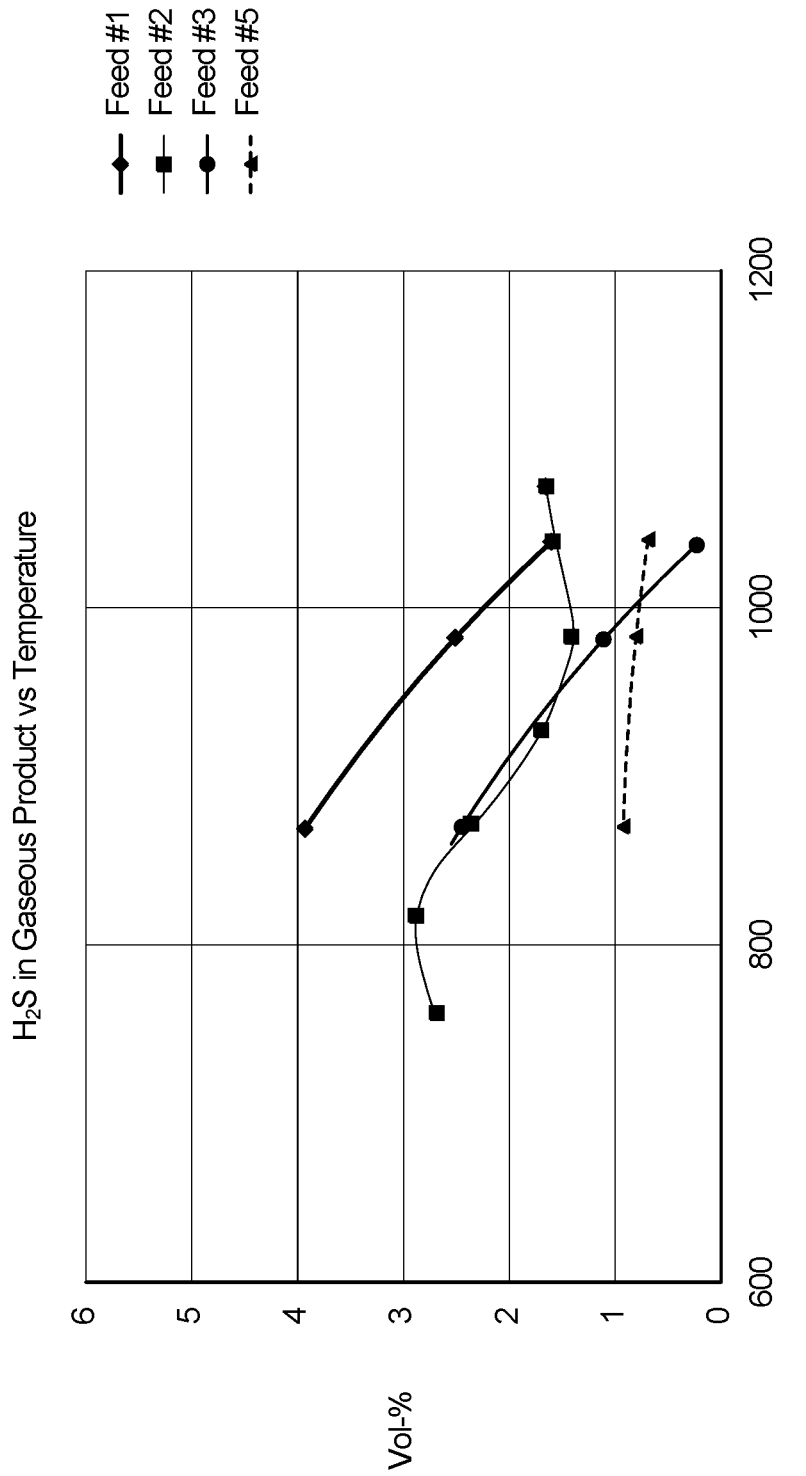
FIG. 3 depicts the relationship between $H_2S$ in the methane-containing gaseous product and the temperature of the DHA reaction, obtained from four feedstocks comprising methane and $H_2S$.

The graphs shown in FIGS. 3-11 were based on data obtained using the sulfided CoMo catalyst and further parameters as described below. FIG. 3 is a graph showing the relationship between the concentration of $H_2S$ in the methane-containing gaseous product and the temperature of the DHA reaction, obtained from FEED #1, FEED #2, FEED #3, and FEED #5, for which the compositions are shown in Table 1. As temperature is increased, the $H_2S$ concentration decreases, not only because $H_2S$ conversion increases, but also because the remaining $H_2S$ becomes diluted with hydrogen produced from the soft oxidation reaction.

Figure 4:
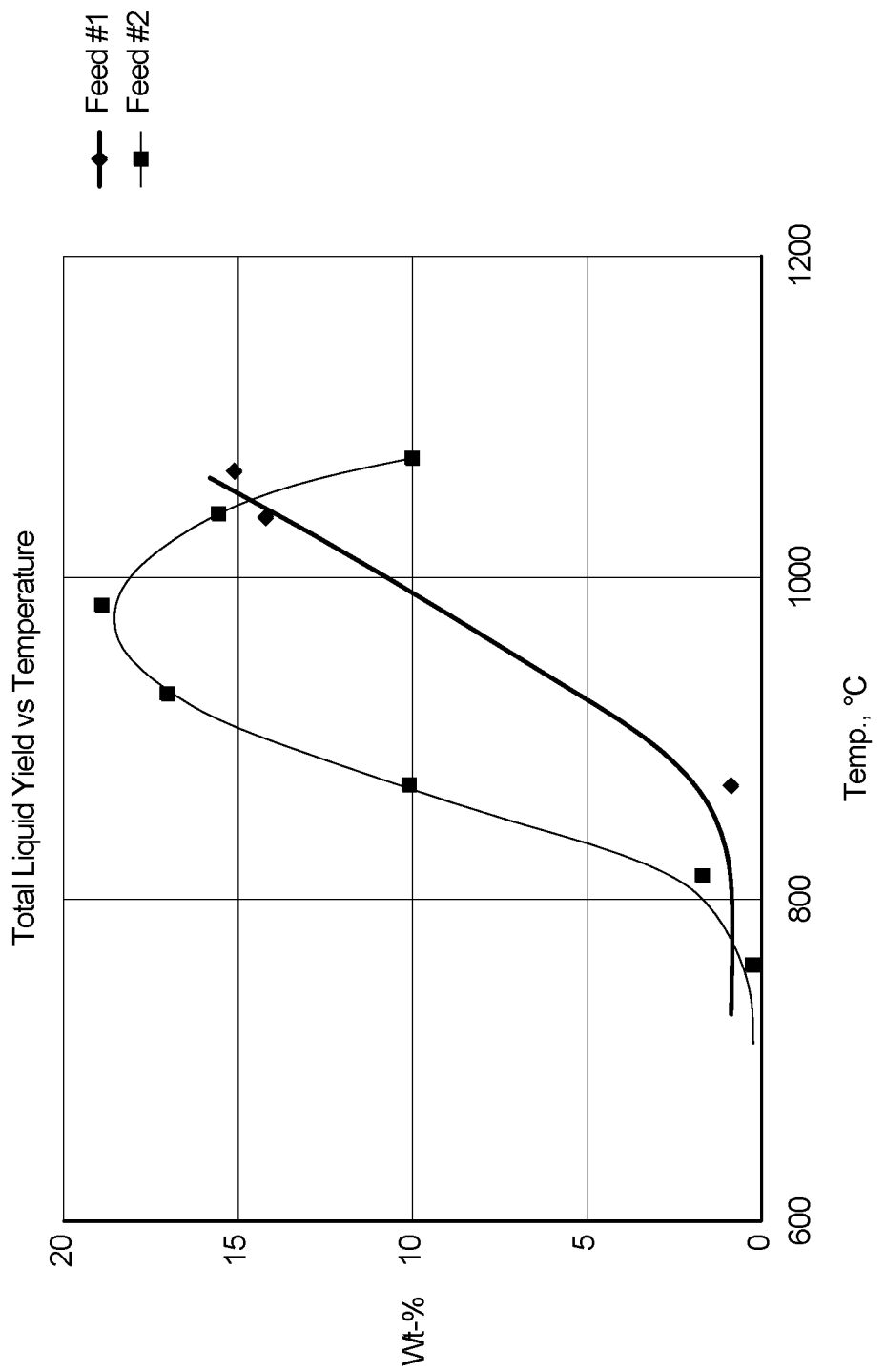
FIG. 4 depicts the relationship between the total liquid product yield and the temperature of the DHA reaction, obtained from two feedstocks comprising methane and $H_2S$.

FIG. 4 is a graph showing the relationship between the total liquid product yield and the temperature of the DHA reaction, obtained from FEED #1 and FEED #2, for which the compositions are shown in Table 1. For the feed comprising ethane and propane, i.e., FEED #2, the peak liquid product yield of 18.5 wt-% was observed at a temperature of 982° C. However, for the feed lacking ethane and propane, i.e., FEED #1, the peak liquid product yield of 14.7 wt-% was observed at a temperature of 1066° C. This illustrates the ability of light hydrocarbons other than methane to become easily converted at relatively low temperatures, via the DHA reaction, to additional liquid hydrocarbons.

Figure 5:
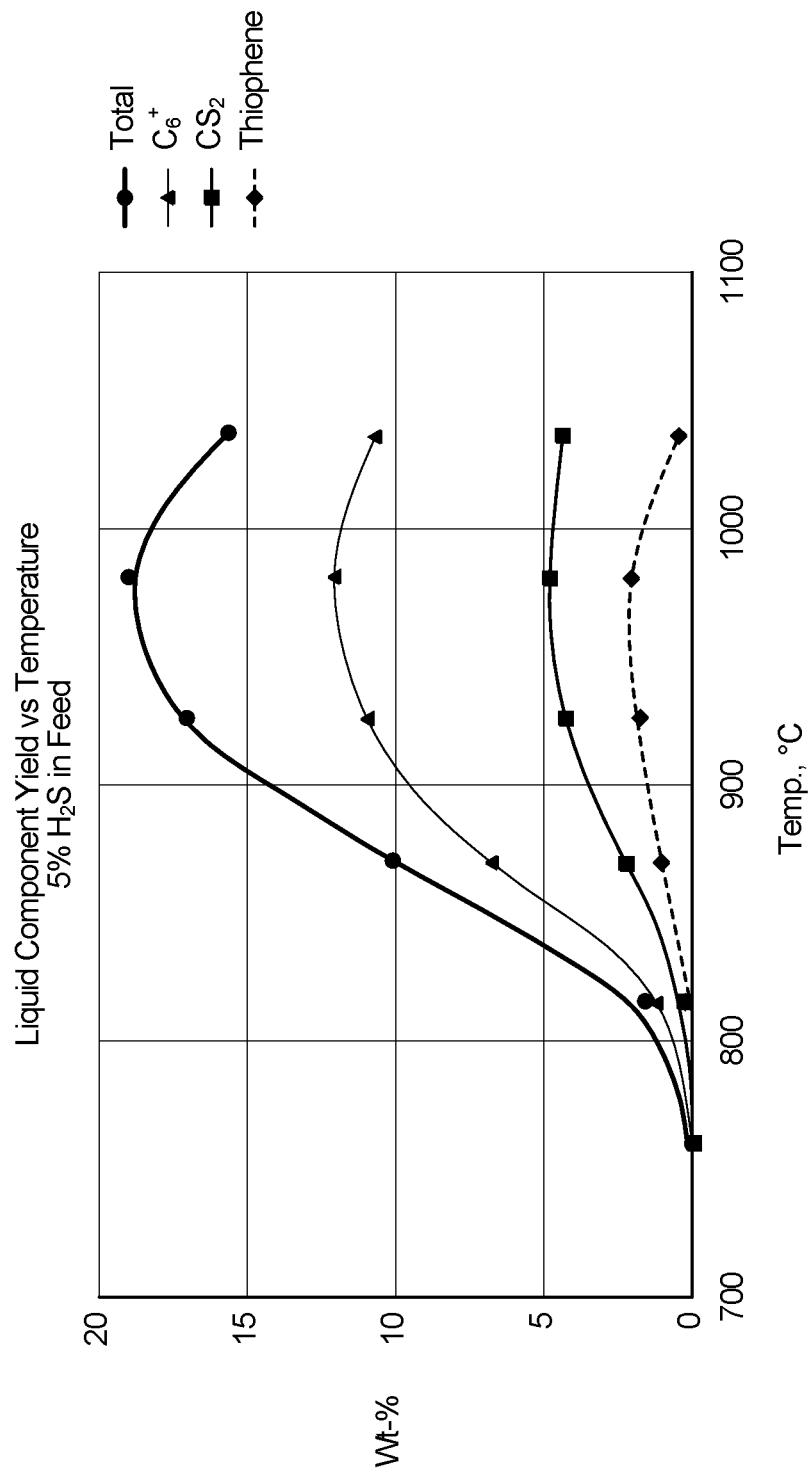
FIG. 5 depicts the relationship between the yields of components of the liquid product and the temperature of the DHA reaction, obtained from a feedstock comprising methane and 5 vol-% $H_2S$.
Figure 6:
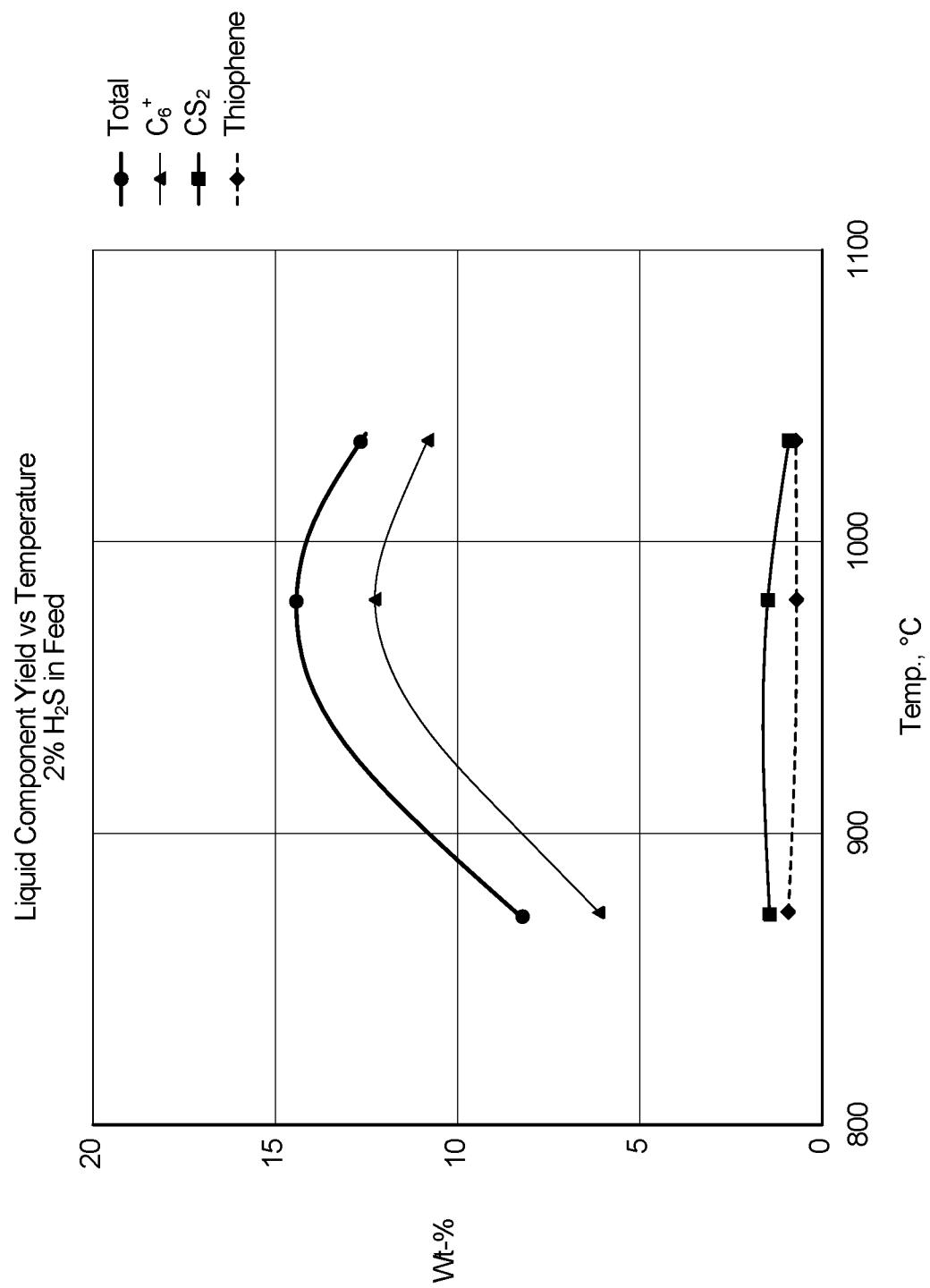
FIG. 6 depicts the relationship between the yields of components of the liquid product and the temperature of the DHA reaction, obtained from a feedstock comprising methane and 2 vol-% $H_2S$.

FIG. 5 is a graph showing the relationship between the yields of components of the liquid product and the temperature of the DHA reaction, obtained from FEED #2, for which the composition is shown in Table 1. As shown, the highest yield of aromatic hydrocarbons ($C_6^+$) was nearly 12 wt-%, the highest yield of CS$_2$ was 4.6 wt-%, and the highest yield of thiophene was 2.2 wt-%. FIG. 6 is a graph showing the same relationship between liquid product component yields and DHA reaction temperature, but in this case obtained from FEED #5, for which the composition is shown in Table 1. As shown, when the concentration of $H_2S$ in the feed was reduced to 2 vol-%, the yield of aromatic hydrocarbons ($C_6^+$) was approximately the same, but the yields of the organic sulfur-containing compounds, namely CS$_2$ and thiophene, were reduced by about 40%, as a result of the reduced concentration of sulfur in the feed.

Figure 7:
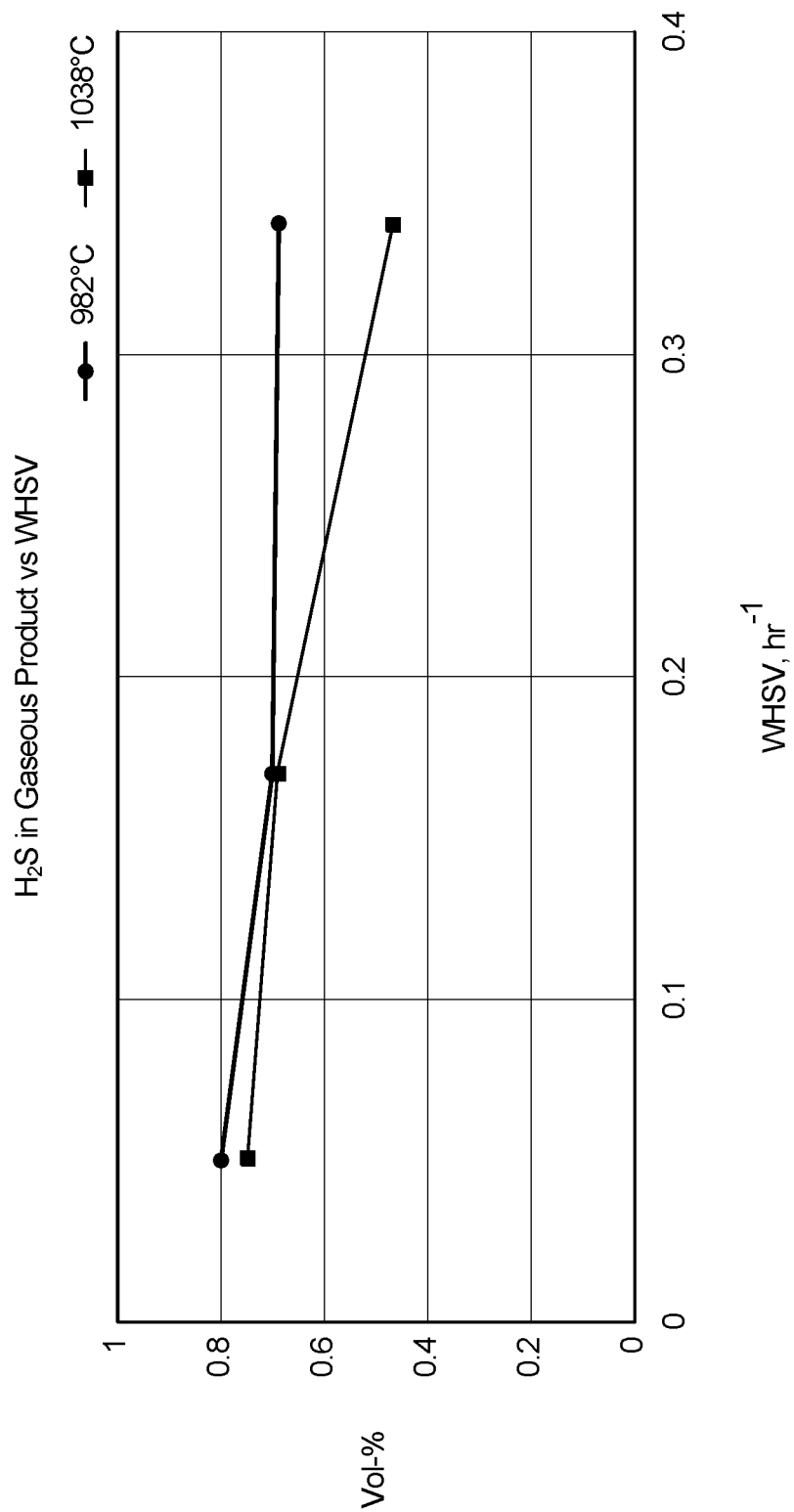
FIG. 7 depicts the relationship between $H_2S$ in the methane-containing gaseous product and the weight hourly space velocity (WHSV) of the DHA reaction, obtained from a feedstock comprising methane and $H_2S$, at temperatures of the DHA reaction of 982° C. and 1038° C.
Figure 8:
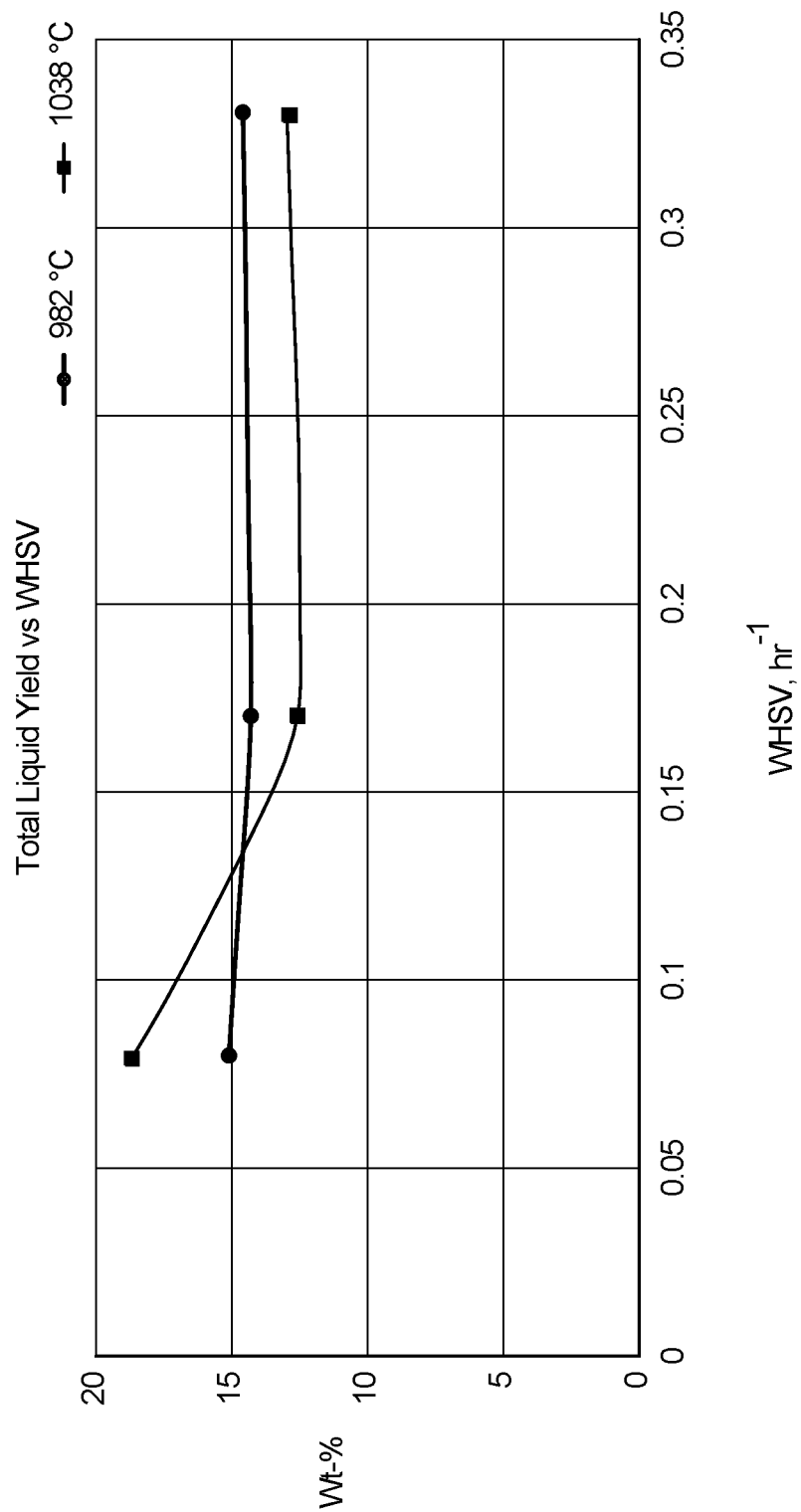
FIG. 8 depicts the relationship between the total liquid product yield and the weight hourly space velocity (WHSV) of the DHA reaction, obtained from a feedstock comprising methane and $H_2S$, at temperatures of the DHA reaction of 982° C. and 1038° C.

FIG. 7 is a graph showing the relationship between $H_2S$ in the methane-containing gaseous product and the weight hourly space velocity (WHSV) of the DHA reaction. FIG. 8 is a graph showing the relationship between the total liquid product yield and the WHSV of the DHA reaction. The data for FIGS. 7 and 8 was obtained from FEED #5, for which the composition is shown in Table 1, at temperatures of the DHA reaction of 982° C. and 1038° C. The $H_2S$ conversion was increased at the higher WHSV values tested, compared to the lower WHSV values. The yields of total liquid product, at all WHSV values tested, were approximately the same at 982° C. The higher space velocities have the potential to minimize the formation of coke that causes catalyst deactivation, and therefore such space velocities can be used to realize advantages in certain cases, without loss of $H_2S$ conversion.

Figure 9:
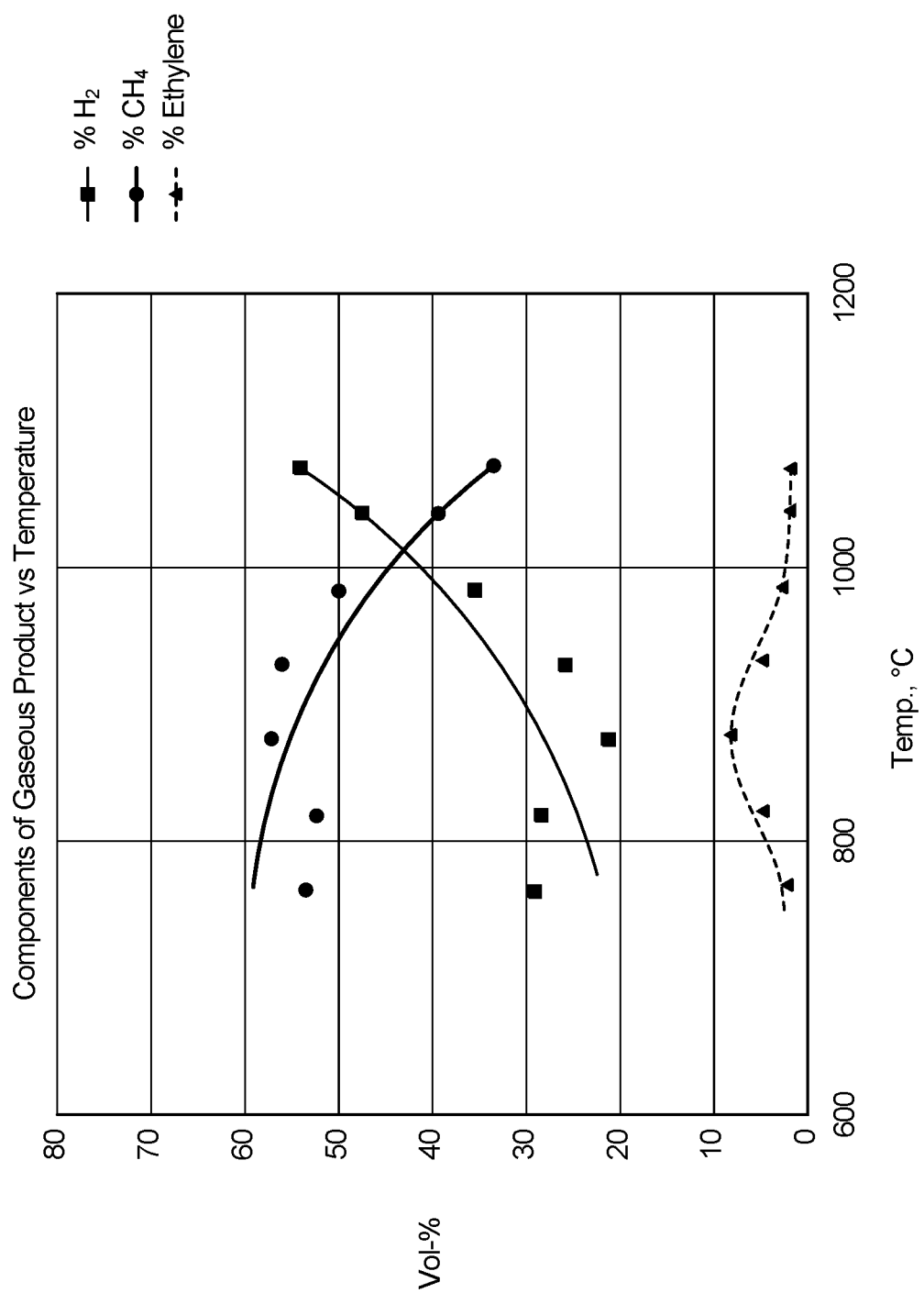
FIG. 9 depicts the relationship between the composition of the gaseous product and the temperature of the DHA reaction.
Figure 10:
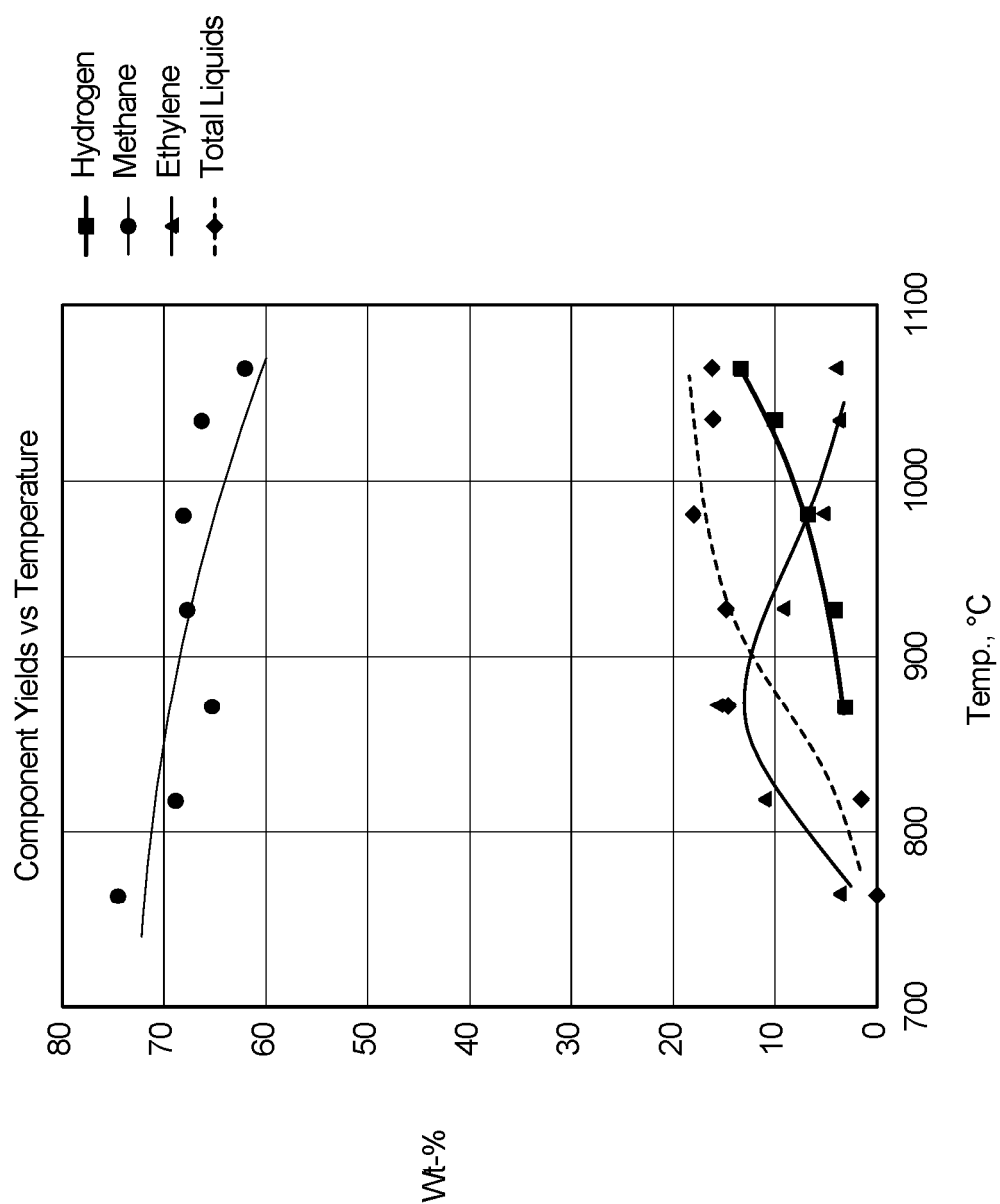
FIG. 10 depicts the relationship between the yields of components of the gaseous and liquid products and the temperature of the DHA reaction.

FIG. 9 is a graph showing the relationship between the composition of the gaseous product, in terms of the vol-% of the various gaseous components, and the temperature of the DHA reaction. FIG. 10 is a graph also showing this relationship, but in terms of wt-% of these components. The data for FIGS. 9 and 10 were obtained from FEED #2, for which the composition is shown in Table 1. As shown in FIGS. 9 and 10, the methane concentration decreased and the hydrogen concentration increased, as temperature was raised and the methane, as well as the other hydrocarbons ethane and propane, were converted to a greater extent in the DHA reaction. This conversion resulted in the formation of ethylene, aromatic hydrocarbons, and thiophene. With respect to aromatic hydrocarbons, typically benzene is the most predominant component, whereas the production of increasing amounts of the C10 bicyclic aromatic hydrocarbon naphthalene provides an indication of coking as aromatization is increased and hydrogen is lost. Table 7 below shows how the weight ratio of benzene to naphthalene varied as a function of DHA reaction temperature. At 926° C., this ratio was very high, but as the temperature increases to 1038° C., most of the aromatic hydrocarbons were naphthalene. The results in Table 7 were obtained from FEED #2, for which the composition is shown in Table 1. However, this effect would be different for different feed compositions and different DHA reaction conditions (e.g., different WHSV values).

TABLE 7

Benzene/Naphthalene wt. Ratio, FEED #2, 150 kPa, 0.14 hr$^{-1}$ WHSV, sulfided CoMo

| DHA Reaction Temperature, ° C. | Benzene/Naphthalene weight ratio |
|---|---|
| 926 | 170 |
| 982 | 26 |
| 1038 | 0.14 |

Figure 11:
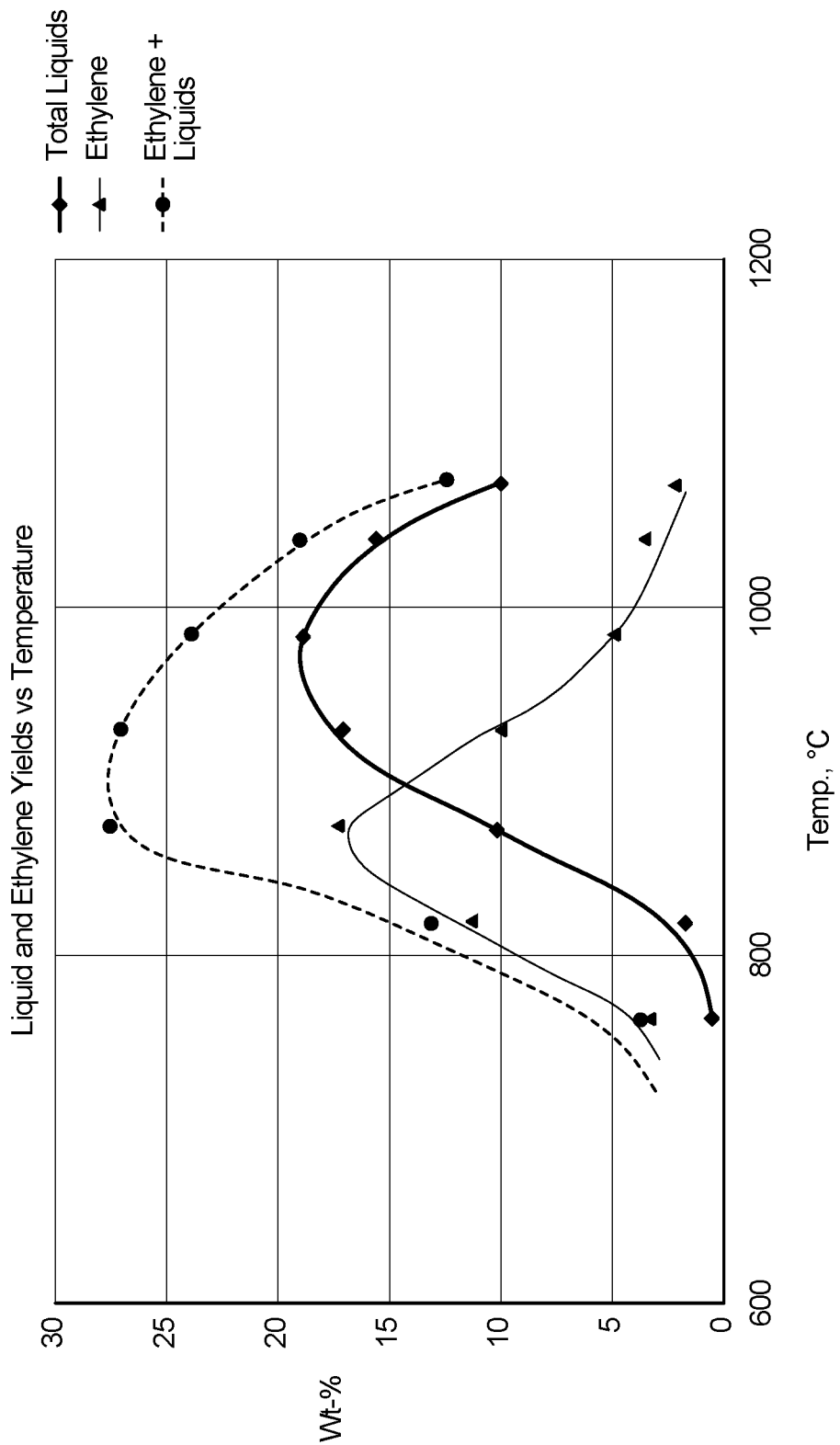
FIG. 11 depicts the relationship between the total liquid product and ethylene yields and the temperature of the DHA reaction.

FIG. 11 is a graph showing the relationship between the total liquid product and ethylene yields and the temperature of the DHA reaction, using data obtained from FEED #2, for which the composition is shown in Table 1. An interesting discovery associated with this work was that a significant amount of ethylene was produced with the benzene and $CS_2$. A trailing oligomerization reactor, operating at about 150° C. with a strong acid catalyst can have the potential to polymerize the ethylene, producing aromatic hydrocarbons such as ethyl benzene, thereby advantageously increasing both the liquid product yield and aromatic hydrocarbon yield. An important consideration is to operate ethylene oligomerization at a sufficiently low temperature to avoid reconverting $CS_2$ back to $H_2S$. Given the potential increase single-pass conversion to liquids, this concept is further illustrative of the commercial viability of the technology.

Overall, aspects of the invention are directed to processes and systems for converting sour methane, e.g., feedstocks comprising methane and $H_2S$, via both soft oxidation and methane dehydroaromatization (DHA) to gaseous and liquid products having higher value. These are namely a "sweetened" (lower $H_2S$ containing) gaseous product and an aromatic hydrocarbon-containing liquid product having organic sulfur compounds. The sulfur can be removed from this product, if desired, using hydroprocessing (e.g., by blending with refinery hydrodesulfurization feedstocks on an industrial scale). The processes and systems exhibit a number of advantages as described above, which include simplicity of operation and the ability to economically upgrade feedstocks that are conventionally flared. Those having skill in the art, with the knowledge gained from the present disclosure, will recognize that various changes can be made to these processes and systems, in attaining these and other advantages, without departing from the scope of the present disclosure. As such, it should be understood that the features of the disclosure are susceptible to modification, alteration, changes, or substitution without departing from the scope of this disclosure. The specific embodiments illustrated and described herein are for illustrative purposes only, and not limiting of the invention as set forth in the appended claims.

The invention claimed is:

1. A methane dehydroaromatization (DHA) process comprising:
    contacting a feedstock comprising methane and $H_2S$ with a DHA catalyst comprising $MoS_2$ or sulfided CoMo to produce a DHA effluent,
    recovering from the DHA effluent a liquid product comprising one or more aromatic hydrocarbons and one or more organic sulfur compounds including $CS_2$, and
    hydroprocessing the liquid product to convert at least a portion of the $CS_2$ to $H_2S$,
    wherein the methane is present in the feedstock at a concentration of at least about 50 vol-%,
    wherein the $H_2S$ is present in the feedstock at a concentration from 1 vol-% to about 25 vol-%, and
    wherein the contacting is carried out under DHA conditions including a temperature from about 900° C. to about 1000° C., an absolute pressure from about 30 kPa to about 2.1 MPa, and a weight hourly space velocity from about 0.05 to about 5 hr$^{-1}$.

2. The process of claim 1, wherein the one or more aromatic hydrocarbons include benzene and the one or more organic sulfur compounds further include thiophene.

3. The process of claim 1, wherein the feedstock comprises sour natural gas.

4. The process of claim 3, wherein the feedstock further comprises a methane-containing gaseous recycle.

5. The process of claim 1, wherein a methane-containing gaseous product is recovered from the DHA effluent.

6. The process of claim 5, wherein the DHA catalyst is contained in a DHA reactor, the process further comprising:
    withdrawing the DHA effluent from the DHA reactor and feeding at least a portion of the DHA effluent to a separator to produce the liquid product and the methane-containing gaseous product.

7. The process of claim 5, further comprising separating $H_2S$ from the methane-containing gaseous product to provide an $H_2S$-depleted methane product.

8. The process of claim 5, wherein the DHA catalyst is contained in a DHA reactor, the process further comprising:
withdrawing the DHA effluent from the DHA reactor and feeding at least a portion of the DHA effluent to an ethylene oligomerization (EO) reactor containing an EO catalyst,
withdrawing an EO effluent from the EO reactor, and
feeding at least a portion of the EO effluent to a separator to produce the liquid product and the methane-containing gaseous product.

9. The process of claim 1, wherein a single pass yield of $CS_2$ in the DHA reaction stage is from about 1% to about 15%.

10. The process of claim 1, wherein the DHA catalyst comprises greater than about 30 wt-% $MoS_2$.

11. A process for sweetening of a feedstock comprising methane and $H_2S$, the process comprising:
in a dehydroaromatization (DHA) reaction stage, contacting at least a portion of the feedstock with a DHA catalyst to provide a DHA effluent,
in a separation stage, separating at least a portion of the DHA effluent to provide
(i) a liquid product comprising one or more aromatic hydrocarbons and one or more organic sulfur compounds including $CS_2$, and
(ii) a methane-containing gaseous product,
in a gas purification stage, separating $H_2S$ from the methane-containing gaseous product to provide
(iii) a sweetened methane product and
(iv) a methane-containing gaseous recycle comprising said $H_2S$
recycling at least a portion of said methane-containing gaseous recycle to said DHA reaction stage, and
hydroprocessing the liquid product to convert at least a portion of the $CS_2$ to $H_2S$,
wherein the DHA reaction stage is carried out at an absolute pressure from about 100 kPa to about 300 kPa, and
wherein $H_2S$ is present in the feedstock at a concentration from 1 vol-% to about 25 vol-%.

12. The process of claim 11, wherein the overall $H_2S$ conversion in the process is from about 50% to about 99%.

13. A process for sweetening of a feedstock comprising methane and $H_2S$, the process comprising:
in a dehydroaromatization (DHA) reaction stage, contacting at least a portion of the feedstock with a DHA catalyst to provide a DHA effluent;
in a separation stage, separating at least a portion of the DHA effluent to provide
(i) a liquid product comprising one or more aromatic hydrocarbons and one or more organic sulfur compounds including $CS_2$, and
(ii) a sweetened methane-containing gaseous product, and
Hydroprocessing the liquid product to convert at least a portion of the $CS_2$ to $H_2S$,
wherein the DHA reaction stage is carried out at an absolute pressure from about 100 kPa to about 300 kPa, and
wherein the $H_2S$ is present in the feedstock at a concentration from 1 vol-% to about 25 vol-%.

14. A methane dehydroaromatization (DHA) process comprising:
contacting a feedstock comprising methane and $H_2S$ with a DHA catalyst to produce a DHA effluent,
recovering from the DHA effluent a liquid product comprising one or more aromatic hydrocarbons and one or more organic sulfur compounds including $CS_2$, and
hydroprocessing the liquid product to convert at least a portion of the $CS_2$ to $H_2S$,
wherein the methane is present in the feedstock at a concentration of at least about 50 vol-% and the $H_2S$ is present in the feedstock at a concentration from 1 vol-% to about 25 vol-%.

15. The process of claim 14, further comprising blending the liquid product with a refinery hydrodesulfurization feedstock before hydroprocessing.

16. The process of claim 14, wherein the one or more aromatic hydrocarbons include benzene and the one or more organic sulfur compounds further include thiophene.

17. The process of claim 14, wherein a methane-containing gaseous product is recovered from the DHA effluent.

18. The process of claim 17, wherein the DHA catalyst is contained in a DHA reactor, the process further comprising:
withdrawing the DHA effluent from the DHA reactor and feeding at least a portion of the DHA effluent to a separator to produce the liquid product and the methane-containing gaseous product.

19. The process of claim 17, wherein the DHA catalyst is contained in a DHA reactor, the process further comprising:
withdrawing the DHA effluent from the DHA reactor and feeding at least a portion of the DHA effluent to an ethylene oligomerization (EO) reactor containing an EO catalyst,
withdrawing an EO effluent from the EO reactor, and
feeding at least a portion of the EO effluent to a separator to produce the liquid product and the methane-containing gaseous product.

* * * * *